US012760342B2

(12) United States Patent
Ma et al.

(10) Patent No.: US 12,760,342 B2
(45) Date of Patent: Oct. 13, 2026

(54) BACILLUS SUBTILIS GENETICALLY ENGINEERED BACTERIUM FOR PRODUCING TAGATOSE AND METHOD FOR PREPARING TAGATOSE

(71) Applicant: TIANJIN YEAHE BIOTECHNOLOGY CO., LTD., Tianjin (CN)

(72) Inventors: Yanhe Ma, Tianjin (CN); Ting Shi, Tianjin (CN); Yunjie Li, Tianjin (CN); Pingping Han, Tianjin (CN); Yuan Li, Tianjin (CN)

(73) Assignee: Tianjin Yeahe Biotechnology Co., Ltd., Tianjin (CN)

( * ) Notice: Subject to any disclaimer, the term of this patent is extended or adjusted under 35 U.S.C. 154(b) by 233 days.

(21) Appl. No.: 18/260,333

(22) PCT Filed: Jul. 28, 2021

(86) PCT No.: PCT/CN2021/108983
§ 371 (c)(1),
(2) Date: Jul. 4, 2023

(87) PCT Pub. No.: WO2022/148008
PCT Pub. Date: Jul. 14, 2022

(65) Prior Publication Data

US 2024/0254527 A1 Aug. 1, 2024

(30) Foreign Application Priority Data

Jan. 5, 2021 (CN) ......................... 202110006046.4

(51) Int. Cl.

| | |
|---|---|
| ***C12P 19/02*** | (2006.01) |
| ***C12N 9/10*** | (2006.01) |
| ***C12N 9/16*** | (2006.01) |
| ***C12N 9/90*** | (2006.01) |
| ***C12N 11/00*** | (2006.01) |
| ***C12N 15/75*** | (2006.01) |

(52) U.S. Cl.
CPC ............ *C12P 19/02* (2013.01); *C12N 9/1051* (2013.01); *C12N 9/16* (2013.01); *C12N 9/90* (2013.01); *C12N 11/00* (2013.01); *C12N 15/75* (2013.01); *C12Y 204/01001* (2013.01); *C12Y 301/03* (2013.01); *C12Y 501/03* (2013.01); *C12Y 503/01009* (2013.01); *C12Y 504/02002* (2013.01)

(58) Field of Classification Search
CPC ........ C12P 19/02; C12P 19/24; C12N 9/1051; C12N 9/16; C12N 9/90; C12N 11/00; C12N 15/75; C12N 9/1205; C12N 15/52; C12N 9/92; C12Y 204/01001; C12Y 301/03; C12Y 501/03; C12Y 503/01009; C12Y 504/02002; C12Y 207/01101; C12R 2001/125
See application file for complete search history.

(56) References Cited

U.S. PATENT DOCUMENTS

| | | | | |
|---|---|---|---|---|
| 11,180,785 B2 * | 11/2021 | Yang | .................... | C12N 9/1205 |
| 2008/0124771 A1 | 5/2008 | Kim et al. | | |
| 2010/0041106 A1 | 2/2010 | Kim et al. | | |

FOREIGN PATENT DOCUMENTS

| | | |
|---|---|---|
| CN | 103451141 A | 12/2013 |
| CN | 104962546 A | 6/2015 |
| CN | 105899660 A | 8/2016 |
| CN | 106399427 A | 2/2017 |
| CN | 107988286 A | 5/2018 |
| CN | 109666620 A | 4/2019 |
| CN | 112342179 A | 2/2021 |
| EP | 3733843 A1 | 4/2020 |
| JP | 2010510776 A | 4/2010 |
| WO | 2020081959 A1 | 4/2020 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Zhang et al., Multigene disruption in undomesticated Bacillus subtilis ATCC 6051a using the CRISPR/Cas9 system. Scientific Reports, 2016, 6:27943, pp. 1-11 (Year: 2016).*
European Patent Office, Supplementary European Search Report, EP Patent Application No. 21917051.1, dated Jul. 9, 2025, DE.

(Continued)

*Primary Examiner* — Ganapathirama Raghu
(74) *Attorney, Agent, or Firm* — Reichel Stohry Dean LLP; Natalie J. Dean

(57) ABSTRACT

Provided are a *Bacillus subtilis* genetically engineered bacterium for producing tagatose and a method for preparing tagatose. The genetically engineered bacterium comprises constructing thermostable α-glucan phosphorylases, thermostable glucose phosphomutases, thermostable glucose phosphate isomerases, thermostable 6-tagatose phosphate epimerases, and thermostable 6-tagatose phosphate phosphatases which are independently expressed or co-expressed. The usage of the genetically engineered bacterium can effectively convert starch into tagatose. Compared with existing methods for producing tagatose, the method has advantages such as suitability for whole-cell recycling, high safety, high yield, simple production process, low cost, and easiness in large-scale preparation.

19 Claims, 6 Drawing Sheets

Specification includes a Sequence Listing.

(56) References Cited

OTHER PUBLICATIONS

International Searching Authority, International Search Report, International Application No. PCT/CN2021/108983, dated Sep. 29, 2021, CN.

International Searching Authority, Written Opinion of the International Searching Authority, International Application No. PCT/CN2021/108983, dated Sep. 29, 2021, CN.

Morimoto et al., Enhanced Recombinant Protein Productivity by Genome Reduction in Bacillus subtilis, DNA Research (15): 73-81 (2008), Oxford University Press, GB.

Cheon et al., Characterization of L-Arabinose Isomerase in Bacillus subtilis, a GRAS Host, for the Production of Edible Tagatose, Food Biotechnology 23(9): 8-16 (2009), Taylor and Francis Ltd., US.

Liu et al., Efficient production of extracellular pullulanase in Bacillus subtilis ATCC6051 using the host strain construction and promoter optimization expression system, Microbial Cell Factories 17(163): 1-12 (2018).

* cited by examiner

BACILLUS SUBTILIS GENETICALLY ENGINEERED BACTERIUM FOR PRODUCING TAGATOSE AND METHOD FOR PREPARING TAGATOSE

PRIORITY

The present application is related to, claims the priority benefit of, and is a 35 U.S.C. 371 national stage application of International Patent Application No. PCT/CN2021/108983 filed Jul. 28, 2021, which is related to and claims priority to Chinese Patent Application No. 202110006046.4 filed Jan. 5, 2021. The content of each of the aforementioned priority applications is hereby expressly incorporated in its entirety into this disclosure by reference.

FIELD OF THE INVENTION

The present invention relates to the field of bioengineering technology, and in particular to genetically engineered bacterium for production of tagatose and a method for producing tagatose.

BACKGROUND OF THE INVENTION

Tagatose is a rare naturally occurring monosaccharide, a ketose form of galactose, a differential isomer of fructose. The sweetness of tagatose is similar to that of sucrose, and its calories are only one-third of that of sucrose, so it is called a low-calorie sweetener. Natural tagatose is mainly found in dairy products such as yogurt and milk powder. Tagatose offers a very fresh and pure sweetness, with a taste profile similar to fructose. Studies have shown that tagatose has important physiological functions such as low calorie, low glycemic index, anti-caries, anti-oxidation, prebiotics, improvement of intestinal function, immune regulation, and drug precursors. It can be widely used in food, beverages, medicine, health care and other fields, and has huge economic value (Oh D-K: Tagatose: properties, applications, and biotechnological processes. App. Microbiol. Biotechnol. 2007, 76:1-8).

In 2001, the US Food and Drug Administration (FDA) confirmed the safety of tagatose and approved it as a GRAS (Generally Regarded As Safe) product. FDA approved tagatose as a tooth-friendly ingredient in December 2002, and as a food additive in October 2003, and can be used as a sweetener in the food and beverage industry and the pharmaceutical field. In 2001, the Joint FAO/WHO Expert Committee on Food Additives (JECFA) recommended Tagatose as a new low-calorie sweetener that can be used as a food additive. At the 63rd meeting in 2004, it was stated that there was no need to limit the Acceptable Daily Intake (ADI) for tagatose and that the "unspecified" ADI was assigned in the JECFA Safest List of Arrangable Food Components. Tagatose was approved for marketing in Korea in 2003, Oceania (Australia and New Zealand) in 2004 and in the EU in 2005, where tagatose was officially approved in the EU as a new food component without any restrictions on its use in December 2005. China also approved tagatose as a new food ingredient in May 2014. Currently, tagatose has been approved by more than 30 countries worldwide as well as by WHO/FAO and the Codex Alimentarius Commission, and there are no restrictions on its permitted daily intake or use.

The production methods of tagatose mainly include chemical synthesis and biotransformation. Generally, it is made by isomerization reaction by chemical method or biological transformation using galactose as raw material.

The chemical synthesis method uses soluble alkali metal salts or alkaline earth metal salts as catalysts to induce the formation of tagatose from galactose under alkaline conditions and the formation of metal hydroxide-tagatose complexes, which are then neutralized with acid to obtain tagatose. The chemical method has high energy consumption, complex products, difficult purification, many side reactions, and chemical pollution. The biological method uses galactitol or galactose, which is catalyzed by enzymes or microorganisms to convert the corresponding substrate into tagatose. Galactitol is expensive and limited in source, making it unsuitable as a raw material for industrial production. The current mainstream production method for tagatose is to produce pure tagatose through isomerisation of galactose, desalination, decolourisation, separation, concentration and crystallisation. However, this method is also flawed in that galactose is not fully converted to tagatose and the end product is a mixture of galactose and tagatose, resulting in a complex tagatose separation process, low conversion rates and high separation costs, while the price of raw galactose is not cheap, and the final tagatose is expensive to produce. (Rhimi M, Aghajari N, Juy M, Chouayekh H, Maguin E, Haser R, Bejar S: Rational design of *Bacillus stearothermophilus* US1001-arabinose isomerase: Potential applications for d-tagatose production. Biochim. 2009, 91:650-653. Oh H-J, Kim H-J, Oh D-K: Increase in d-tagatose production rate by site-directed mutagenesis of 1-arabinose isomerase from *Geobacillus thermodenitrificans*. Biotechnol. Lett. 2006, 28:145-149. Bosshart A, Hee C S, Bechtold M, Schirmer T, Panke S: Directed divergent evolution of a thermostable D-tagatose epimerase towards improved activity for two hexose substrates. ChemBioChem 2015, 16:592-601.)

C J Korea invented the multi-enzyme catalyzed conversion of fructose into tagatose technology (Oh D K, HONG S H, Lee S H: Aldolase, aldolase mutants and tagatose using the same production methods and compositions for production. WO 2015016544A1), including fructokinase, aldolase, and phytase, but the production of fructose 6-phosphate from fructose requires ATP to phosphorylate fructose as a substrate, and the addition of expensive ATP leads to high cost of tagatose production, which is not of industrial production value (TW107111500, US20160186162A1). C J Korea developed and modified hexuronate 4-epimerase to convert fructose to tagatose (CN105431541B, CN109415715A), the modified hexuronate 4-epimerase enzyme activity is extremely low and does not have industrial application. C J Korea also developed a novel source of 6-phosphotagatose phosphatase and applied it to the conversion of substrates such as starch, maltodextrin and sucrose to produce tagatose (WO2018004310A1, CN 109790524 A), but the 6-phosphotagatose phosphatase enzyme activity is extremely low and is not industrially applicable at this stage.

Tianjin Institute of Industrial Biotechnology, Chinese Academy of Sciences has established a new route for the in vitro multi-enzyme synthesis of tagatose using cheap corn starch, maltodextrin and sucrose as raw materials, which fundamentally changed the existing production process of tagatose (CN106399427A). On this basis, Tianjin Institute of Industrial Biotechnology, Chinese Academy of Sciences used cheap corn starch, cellulose, maltodextrin and sucrose as raw materials to prepare tagatose using whole-cell catalysis (CN107988286A), a process that reduces multiple enzyme purification process steps, reduces production costs and environmental pollution, and improves tagatose yields. However, the host for fermentation production of the key enzyme in this method is *E. coli* BL21 (DE3), which is not suitable as a production strain for industrial production of enzymes related to food preparation production. In addition to this, the in vitro enzyme isolation and purification steps are cumbersome, the enzyme recovery rate is low, recycling is difficult, and the production cost cannot be further reduced to achieve industrial mass production application of highly concentrated products.

Therefore, there is an urgent need to develop a new method for whole cell recycling, high safety, high yield, simple production process, low cost and suitable for high substrate concentration feeding and high product tagatose output, which is easy to prepare tagatose on a large scale.

SUMMARY OF THE INVENTION

Aiming at the problems existing in the existing multi-enzyme catalyzed method for production of tagatose, such as the fact that *E. coli* is not conducive to the industrial production of food preparations, the cumbersome purification step, the low utilization rate of enzyme recycling and the difficulty of recycling, and the problem of feeding low concentration substrate starch, the main purpose of the present invention is to provide a method for producing high-concentration tagatose by catalyzing high-concentration starch using whole cells of *Bacillus subtilis.*

The present invention first provides a *Bacillus subtilis* genetically engineered bacterium for producing tagatose, which is a *Bacillus subtilis* genetically engineered bacterium co-expressing an α-glucan phosphorylase gene, a glucose phosphomutase gene, a glucose phosphate isomerase gene, a 6-tagatose phosphate epimerase gene, and a 6-tagatose phosphate phosphatase gene, or a mixture of *Bacillus subtilis* genetically engineered bacteria respectively expressing an α-glucan phosphorylase gene, a glucose phosphomutase gene, a glucose phosphate isomerase gene, a 6-tagatose phosphate epimerase gene, and a 6-tagatose phosphate phosphatase gene.

The principle of the above technical solution is to make full use of relevant catalytic pathways to express and realize effective catalytic reactions at the level of living cells, which includes conversion of the substrate starch to the intermediate glucose-1-phosphate (GIP) by α-glucan phosphorylase in the presence of inorganic phosphorus; isomerization of the intermediate glucose-1-phosphate (GIP) to another intermediate glucose-6-phosphate (G6P) by glucose phosphomutase; isomerization of the intermediate glucose-6-phosphate (G6P) to another intermediate fructose-6-phosphate (F6P) by glucose phosphate isomerase; epimerization of the intermediate fructose-6-phosphate (F6P) to another intermediate tagatose 6-phosphate (T6P) by 6-tagatose phosphate epimerase; and removal of the phosphate group from the intermediate tagatose-6-phosphate (T6P) to the product tagatose by 6-tagatose phosphate phosphatase.

Various strains of *Bacillus subtilis* known in the art can be used as starting strains for the invention, such as *Bacillus subtilis* 168, DB104, WB800, WB600, SCK6, 1A751, ATCC6051a, ATCC6051 and others. Preferably, the *Bacillus subtilis* starting strain is a protease-knockout strain of *Bacillus subtilis* strain, e.g., WB800, WB600, SCK6, 1A751, etc. More preferably, the *Bacillus subtilis* strain is SCK6.

In specific embodiments, the genetically engineered bacterium comprises an expression vector co-expressing α-glucan phosphorylase, glucose phosphomutase, glucose phosphate isomerase, 6-tagatose phosphate epimerase, and 6-tagatose phosphate phosphatase, or the genetically engineered bacterium is a mixture of a genetically engineered bacterium comprising an expression vector for α-glucan phosphorylase, a genetically engineered bacterium comprising an expression vector for glucose phosphomutase, a genetically engineered bacterium comprising an expression vector for glucose phosphate isomerase, a genetically engineered bacterium comprising an expression vector for 6-tagatose phosphate epimerase and a genetically engineered bacterium comprising an expression vector for 6-tagatose phosphate phosphatase.

Preferably, the various enzymes are of the thermostable type, i.e., thermostable α-glucan phosphorylase, thermostable glucose phosphomutase, thermostable glucose phosphate isomerase, thermostable 6-tagatose phosphate epimerase, and thermostable 6-tagatose phosphate phosphatase. The use of thermostable enzymes has an advantage over non-heat resistant room temperature enzymes in terms of strain inactivation, i.e., using the thermostable enzymes, the strains can be inactivated by heat treatment at the end of fermentation while the enzymes associated with tagatose synthesis remain active, thus allowing a mixture of inactivated strains to be used for tagatose production, which is more suitable for industrial 45 applications. If the relevant room temperature enzyme is used, then at the end of the fermentation production it is necessary to obtain the pure enzyme by crushing the bacterium and an enzyme purification step before the relevant enzyme can be obtained for the production of tagatose.

Specifically, said thermostable α-glucan phosphorylase refers to an enzyme having the function of phosphorylating starch to glucose-1-phosphate (GIP) above 40 °C, above 45 °C, above 50 °C, above 55 °C, above 60 °C, above 65 °C, above 70 °C, above 75 °C, or above 80 °C Further preferably, said thermostable α-glucan phosphorylase is derived from thermophilic microorganisms such as *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Thermus thermophilus, Methanothermobacter marburgensis, Archaeoglobus profundus*, etc; or said thermostable α-glucan phosphorylase has an amino acid sequence having at least 70%, preferably at least 80%, more preferably at least 90%, most preferably at least 95% identity to a thermostable α-glucan phosphorylase derived from said thermophilic microorganism. More preferably, said thermostable α-glucan phosphorylase is derived from *Thermococcus kodakarensis.*

Specifically, said thermostable glucose phosphomutase refers to an enzyme that has the function of isomerising glucose-1-phosphate (GIP) to glucose-6-phosphate (G6P) above 40 °C, above 45 °C, above 50 °C, above 55 °C, above 60 °C, above 65 °C, above 70 °C, above 75 °C, or above 80 °C. Further preferably, said thermostable glucose phosphomutase is derived from thermophilic microorganisms, such as *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Thermus thermophilus, Methanothermobacter marburgensis, Archaeoglobus profundus*, etc; or said thermostable glucose phosphomutase has an amino acid sequence having at least 70%, preferably at least 80%, more preferably at least 90%, most preferably at least 95% identity to a thermostable glucose phosphomutase derived from said thermophilic microorganism. More preferably, said thermostable glucose phosphomutase is derived from *Thermococcus kodakarensis.*

Specifically, said thermostable glucose phosphate isomerase refers to an enzyme with the function of isomerising glucose-6-phosphate (G6P) to fructose-6-phosphate (F6P) above 40 °C, above 45 °C, above 50 °C, above 55 °C, above 60 °C, above 65 °C, above 70 °C, above 75 °C, or above 80 °C. Further preferably, said thermostable glucose phosphate isomerase is derived from thermophilic microorganisms, such as *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Thermus thermophilus, Methanothermobacter marburgensis, Archaeoglobus profundus*, etc; or said thermostable glucose phosphate isomerase has an amino acid sequence having at least 70%, preferably at least 80%, more preferably at least 90%, most preferably at least 95% identity to a thermostable glucose phosphate isomerase derived from said thermophilic microorganism. More preferably, said thermostable glucose phosphate isomerase is derived from *Thermus thermophilus.*

Specifically, said thermostable 6-tagatose phosphate epimerase is an enzyme with the function of epimerizing fructose-6-phosphate (F6P) to tagatose 6-phosphate (T6P) above 40 °C, above 45 °C, above 50 °C, above 55 °C, above 60 °C, above 65 °C, above 70 °C, above 75 °C, or above 80 °C. Further preferably, said thermostable 6-tagatose phosphate epimerase is derived from thermophilic microorganisms, such as *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis*, Dietyoglomus *thermophilum, Caldicellulosiruptor kronotskyensis, Clostridium thermocellum, Caldilinea aerophila, Pyrococcus furiosus, Thermus thermophilus, Methanothermobacter marburgensis, Archaeoglobus profundus*, etc; or said thermostable 6-tagatose phosphate epimerase has an amino acid sequence having at least 70%, preferably at least 80%, more preferably at least 90%, most preferably at least 95% identity to a thermostable 6-tagatose phosphate epimerase derived from said thermophilic microorganism. More preferably, said thermostable 6-tagatose phosphate epimerase is derived from *Thermoanaerobacter indiensis.*

Specifically, said thermostable 6-tagatose phosphate phosphatase refers to an enzyme having the function of removing the phosphate group from tagatose 6-phosphate (T6P) to the product tagatose above 40 °C, above 45 °C, above 50 °C, above 55 °C, above 60 °C, above 65 °C, above 70 °C, above 75 °C, or above 80 °C. Further preferably, said thermostable 6-tagatose phosphate phosphatase is derived from thermophilic microorganisms, such as *Geobacillus kaustophilus, Geobacillus stearothermophilus, Thermotoga maritima, Pseudothermotoga thermarum, Thermococcus kodakarensis, Archaeoglobus fulgidus, Thermoanaerobacter indiensis, Dictyoglomus thermophilum, Caldicellulosiruptor kronotskyensis, Clostridium thermocellum, Caldilinea aerophila, Pyrococcus furiosus, Thermus thermophilus, Methanothermobacter marburgensis, Archaeoglobus profundus*, etc; or said thermostable 6-tagatose phosphate phosphatase has an amino acid sequence having at least 70%, preferably at least 80%, more preferably at least 90%, most preferably at least 95% identity to a thermostable 6-tagatose phosphate phosphatase derived from said thermophilic microorganism. More preferably, said thermostable 6-tagatose phosphate phosphatase is derived from *Archaeoglobus fulgidus.*

The present invention accordingly provides an expression vector for the above genetically engineered bacterium comprising the genes for α-glucan phosphorylase, glucose phosphomutase, glucose phosphate isomerase, 6-tagatose phosphate epimerase, and 6-tagatose phosphate phosphatase and enabling co-expression of these genes.

It will be understood by those skilled in the art that the vectors and genetically engineered bacteria covered by the present invention can be prepared by conventional methods known in the art, for example, by constructing by recombinant DNA technology, obtaining α-glucan phosphorylase gene, glucose phosphomutase gene, glucose phosphate isomerase gene, 6-tagatose phosphate epimerase gene, 6-tagatose phosphate phosphatase gene, constructing a recombinant expression vector, and then transferring it into *Bacillus subtilis* by known methods to obtain genetically engineered bacteria.

More preferably, said vector comprises a promoter, a thermalstable α-glucan phosphorylase gene, a thermalstable glucose phosphomutase gene, a thermalstable glucose phosphate isomerase gene, a thermalstable 6-tagatose phosphate epimerase gene, a thermalstable 6-tagatose phosphate phosphatase gene and a terminator. And respectively, said vector expressing α-glucan phosphorylase comprises a promoter, a thermalstable α-glucan phosphorylase gene, and a terminator; said vector expressing glucose phosphomutase comprises a promoter, a thermalstable glucose phosphomutase gene, and a terminator; said vector expressing glucose phosphate isomerase comprises a promoter, a thermalstable glucose phosphate isomerase gene, and a terminator; said vector expressing 6-tagatose phosphate epimerase comprises a promoter, a thermalstable 6-tagatose phosphate epimerase gene, and a terminator; and said vector expressing 6-tagatose phosphate phosphatase comprises a promoter, a thermalstable 6-tagatose phosphate phosphatase gene, and a terminator.

It will be understood by those of skill in the art that various promoters known in the art can be used as promoters of the present invention including, but not limited to, P43 promoter, Py1b promoter, PamyL promoter, Plaps promoter, PhpaII promoter, PamyE promoter, Pgrac promoter, PsacB promoter, PsigX promoter, PaprE promoter, PgroES promoter, etc. Preferably, the promoter of the present invention is PhpaII promoter and Py1b promoter connected in series. Various terminators known in the art can also be used as the terminator in the present invention.

In preferred embodiments, endogenous uracil phosphoribosyltransferase gene, and/or α-amylase gene, and/or sporulating RNA polymerase of factor gene, and/or surface-active peptide synthase subunit 3 gene are inactivated or knocked out in said genetically engineered bacterium. Most preferably, the endogenous uracil phosphoribosyltransferase gene, the α-amylase gene, the sporulating RNA polymerase of factor gene, and the surface-active peptide synthase subunit 3 gene are all inactivated or knocked out in said genetically engineered bacterium. Inactivating or knocking out the above genes can further improve the efficiency of tagatose production by genetically engineered bacterium, specifically because inactivating or knocking out the uracil phosphoribosyltransferase gene may allow the construction of a traceless genetic operating system where subsequent genetic manipulations (i.e. knocking out genes) can be done without introducing exogenous genes such as resistance genes; inactivating or knocking out the α-amylase gene may remove the pathway by which the strain utilizes exogenous starch, preventing the substrate starch for tagatose production from being metabolized by the strain as a carbon source; inactivating or knocking out sporulating RNA polymerase of factor gene may orient the metabolic flow of the strain towards the expression of heterologous protein synthesis associated with tagatose synthesis, while also enabling controlled fermentation of the strain without spore formation; and inactivating or knocking out the surface-active peptide synthase subunit 3 gene may allow for easier control in the fermentation production of the bacterium without producing too much foam. Thus, inactivation or knockout of the above four genes can better facilitate the production of tagatose by genetically engineered bacteria and is therefore the preferred embodiment.

Inactivation or knockout of endogenous genes can be achieved by methods known in the art, preferably by gene editing.

The present invention further provides a method for producing tagatose by utilizing a whole cell of the above genetically engineered bacterium to catalyze starch, comprising the steps of:

(1) fermenting said *Bacillus subtilis* genetically engineered bacterium to obtain whole cells;
(2) subjecting the whole cells of *Bacillus subtilis* obtained in step (1) to a cell membrane permeability treatment to obtain permeable whole cells;
(3) catalyzing starch by utilizing the permeable whole cells obtained in step (2) to produce tagatose, wherein for co-expressing whole cells of *Bacillus subtilis* engineered bacterium, the whole cells are used directly for catalysis, and for whole cells of *Bacillus subtilis* engineered bacterium expressing various enzymes separately, the whole cells are mixed for catalysis.

Preferably, it further comprises immobilizing the *Bacillus subtilis* permeable whole cells obtained in step (2) to obtain immobilized whole cells, or a mixture of immobilized whole cells, which can then be used for catalysis.

In specific embodiments, the preparation of whole cells as described in step (1) is carried out using methods known in the art. Fermentation may be carried out using any medium suitable for exogenous protein expression, including but not limited to LB medium, SR medium, TB medium, etc.

In preferred embodiments, the cell membrane permeability treatment described in step (2) may be by known methods including, but not limited to, heat treatment, addition of organic solvents and/or addition of surfactants, etc. The organic solvents include, but are not limited to, acetone, acetonitrile, etc. Surfactants include but are not limited to cetyltrimethylammonium bromide (CTAB), Tween-80, etc. Preferably, the cell membrane permeability treatment is a heat treatment. The purpose of the permeability treatment of the cell membrane is to allow extracellular starch to pass through the cell membrane and into the cell.

Preferably, said heat treatment temperature is 45 to 100 °C; more preferably, the heat treatment temperature is 70 to 80 °C. Preferably, the heat treatment time is 10 to 100 min; more preferably, the heat treatment time is 50 to 70 min. Preferably, the cell concentration during heat treatment is $OD_{600}$=10 to 300; more preferably, the cell concentration is $OD_{600}$=30 to 150. Also, said heat treatment may be carried out in a bufferless system or a buffered system; preferably, said heat treatment is carried out in a buffered system, said buffer may be HEPES buffer, phosphate buffer, Tris buffer, and acetate buffer, etc. Among these, the phosphate buffer is, for example, a sodium phosphate buffer, a potassium phosphate buffer, etc.

In specific embodiments, the concentration of the substrate starch in the catalyzed reaction system is 50 to 300 g/L; more preferably, the concentration of the substrate starch is 100 to 200 g/L. Preferably, the reaction conditions are: 0.5 to 96 h at pH 5.0 to 8.0 and 40 to 80 °C; more preferably 12 to 60 h at pH 6.5 to 7.5 and 45 to 75 °C; most preferably 12 to 96 h at pH 7.5 and 60 to 70 °C. Said catalysis may be carried out in a bufferless system or a buffered system; preferably, in a buffered system, said buffer may be a HEPES buffer, a phosphate buffer, a Tris buffer, an acetate buffer, etc. Among these, the phosphate buffer is, for example, a sodium phosphate buffer, a potassium phosphate buffer, etc.

Preferably, for the permeable whole cells of *Bacillus subtilis* engineering bacteria expressing various enzymes separately, the mixture comprises permeable whole cells expressing thermostable α-glucan phosphorylase, permeable whole cells expressing thermostable glucose phosphomutase, permeable whole cells expressing thermostable glucose phosphate isomerase, permeable whole cells expressing thermostable 6-tagatose phosphate epimerase; and permeable whole cells expressing thermostable 6-tagatose phosphate phosphatase in a ratio of (0.1-10):(0.1-10):(0.1-10):(0.1-10):(0.1-10); more preferably (0.5-5):(0.5-5):(0.5-5):(0.5-5):(0.5-5), most preferably 1:1:1:1:1.

In specific embodiments, said permeable whole cells are immobilized by resuspending permeable whole cells co-expressing thermostable α-glucan phosphorylase, thermostable glucose phosphomutase, thermostable glucose phosphate isomerase, thermostable 6-tagatose phosphate epimerase, and thermostable 6-tagatose phosphate phosphatase in sodium phosphate or potassium phosphate buffer, adding an appropriate amount of inorganic clay and stirring well. Aqueous polyethyleneimine solution is added to flocculate at room temperature and cross-linked by adding a cross-linking agent. A filter cake layer is obtained by filtration, washed with deionized water and squeezed to prepare into pellets, which are dried to obtain immobilized whole cells.

Said mixture of permeable whole cells are immobilized by resuspending permeable whole cells expressing thermostable α-glucan phosphorylase, permeable whole cells expressing thermostable glucose phosphomutase, permeable whole cells expressing thermostable glucose phosphate isomerase, permeable whole cells expressing thermostable 6-tagatose phosphate epimerase, and permeable whole cells expressing thermostable 6-tagatose phosphate phosphatase in sodium phosphate or potassium phosphate buffer, respectively, adding an appropriate amount of inorganic clay and stirring well. Aqueous polyethyleneimine solution is added to flocculate at room temperature and cross-linked by adding a cross-linking agent. A filter cake layer is obtained by filtration, washed with deionized water and squeezed to prepare into pellets, which are dried to obtain immobilized whole cells.

Where, said inorganic clay includes, but is not limited to, montmorillonite, diatomaceous earth, kaolin and bentonite, etc., preferably, said inorganic clay is diatomaceous earth; said cross-linking agent includes, but is not limited to, glutaraldehyde, trihydroxymethylphosphine, N,N-methylenebisacrylamide, epichlorohydrin, genipin, etc., preferably, said cross-linking agent is glutaraldehyde.

Compared to the prior art, the present invention has the following beneficial effects:

(1) The present invention is the first to use whole cells expressing thermalstable α-glucan phosphorylase, thermalstable glucose phosphomutase, thermalstable glucose phosphate isomerase, thermalstable 6-tagatose phosphate epimerase, and thermalstable 6-tagatose phosphate phosphatase to catalyze the production of tagatose, developing a new method for the simple and easily scalable production of tagatose.

(2) *Bacillus subtilis* is a Generally Recognized as Safe (GRAS) food grade microorganism and does not produce endotoxins. Further, the knockout of the gene encoding α-amylase facilitates the subsequent catalytic application of the substrate starch; the knockout of the gene encoding σF factor of the sporulating RNA polymerase facilitates the subsequent application of the genetically engineered strain for fermentation production in the conversion of the substrate to produce tagatose; the knockout of the gene encoding the surface active peptide synthase subunit 3 facilitates the subsequent application of the genetically engineered strain for fermentation production in the conversion of the substrate to produce tagatose.

(3) In preferred embodiments, by using various thermalstable enzymes, the production of tagatose can be carried out at a higher temperature, which can increase the solubility of the substrate starch. Compared to the prior art, the present invention can achieve the production of tagatose at a higher substrate concentration, which is conducive to improving production efficiency and further reducing production costs.

(4) The transformation reaction of tagatose in the method of the present invention can be carried out in a buffer-free system or a buffer system without the use of a medium containing a carbon source, a nitrogen source, inorganic salts and antibiotics, which on the one hand helps to reduce production costs and on the other hand facilitates the isolation and purification of the product tagatose.

DETAILED DESCRIPTION OF THE INVENTION

Figure 1:
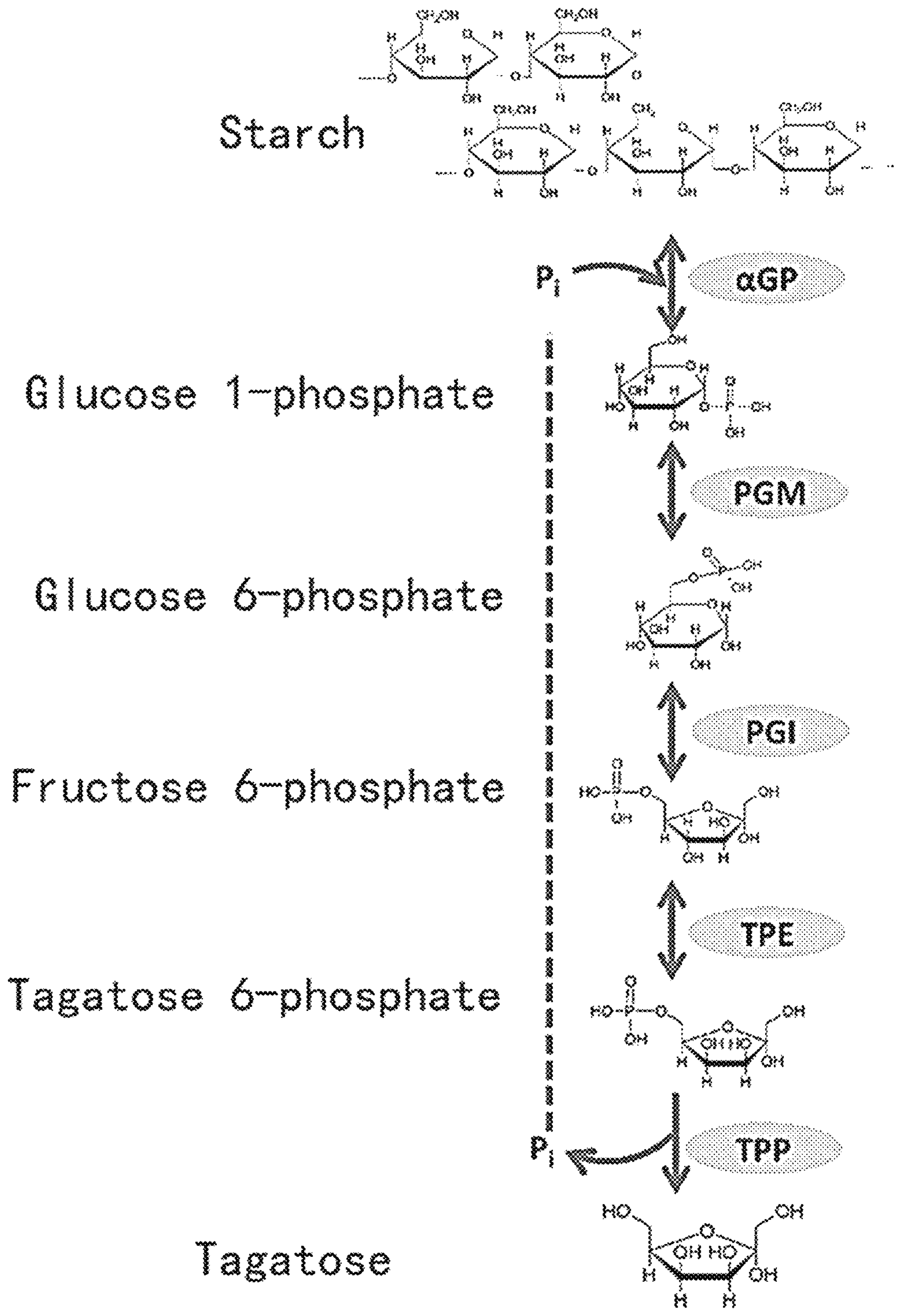
FIG. 1 shows a schematic diagram of the production of tagatose by utilizing whole cells to catalyze starch.

In order to further illustrate the technical means adopted in the present invention and its effects, the technical solutions of the invention are further described below by means of specific embodiments. It should be understood, however, that the embodiments described are exemplary and preferred embodiments only, but do not constitute any limitation on the scope of the invention. It should be understood by those skilled in the art that modifications or substitutions may be made to the details and form of the technical solutions of the invention without departing from the spirit and scope of the invention, but that such modifications or substitutions fall within the scope of protection of the invention.

Example 1 Construction of *Bacillus subtilis* Recombinant Strain SCK8

(1) Construction of Recombinant Integration Vector pSS-Upp-FR

According to the gene sequence of uracil phosphoribosyltransferase coding gene upp derived from *Bacillus subtilis* 168 (NCBI-ProteinID: NP_391570) in the KEGG database, primers were designed. The upstream 500 bp homologous fragment and the downstream 500 bp homologous fragment of the upp coding gene were amplified by PCR, and constructed into integration vector pSS by simple cloning connection method (You, C., Zhang, X. Z., & Zhang, Y. H. (2012). Simple cloning via direct transformation of PCR product (DNA Multimer) to *Escherichia coli* and *Bacillus subtilis*. Appl. Environ. Microbiol., 78(5), 1593-1595. doi: 10.1128/AEM.07105-11) to obtain a recombinant integration vector pSS-upp-FR.

(2) Construction of *Bacillus subtilis* Recombinant Strain SCK8

*Bacillus subtilis* strain SCK6 super competent cells (200 μL) were prepared (Zhang, X. Z., & Zhang, Y. H. P. (2011). Simple, fast and high-efficiency transformation system for directed evolution of cellulase in *Bacillus subtilis*. Microb. Biotechnol., 4(1), 98-105. doi: 10.1111/j.1751-7915.2010.00230.x), and the recombinant integration vector pSS-upp-FR (1 μg) was evenly mixed with *Bacillus subtilis* strain SCK6 super competent cells (200 μL), and then placed in a shaker at 37 °C for 90 min to recover. The bacterial solution was coated on solid medium LB (yeast extract 5 g/L, peptone 10 g/L, sodium chloride 10 g/L) containing chloramphenicol (5 μg/mL), and then placed in a 37 °C incubator for 14 to 16 h.

The positive single-crossover transformant colony grown on the chloramphenicol-resistant plate was picked for colony PCR verification, and those with the two bands of 1000 bp DNA fragment and 2000 bp DNA fragment obtained by PCR amplification (where, the size of the 1000 bp DNA fragment was the fragment size of the upstream and downstream homology arms of the upp coding gene in the vector pSS-upp-FR, the size of the 2000 bp DNA fragment was the size of the fragment on the genome comprising the upstream homology arm of the upp conding gene, the upp conding gene, and the downstream homology arm of the upp conding gene) were positive clones.

Positive clones were picked and transferred to LB medium without adding antibiotics for 8 to 12 h, then 200 μL of the bacterial solution was centrifuged to remove the supernatant, then resuspended in sterile water and coated on a solid plate of 5-FU basic salt medium (40% glucose 20.0 ml/L, 4% glutamine 50.0 mL/L, 0.5% histidine 10.0 mL/L, 1% vitamin B1 1.0 mL/L, 20 mM 5-FU 500 μL/L, 10×spizizen 100.0 mL/L, 1000×trace elements 1.0 mL/L), and placed in a 37 °C incubator for 24 h. The purpose of this step was to promote the intramolecular homologous recombination of positive transformants by culturing in LB medium without adding antibiotics, and then to obtain upp knockout target transformants by screening and culturing in 5-FU basic salt medium.

Several colonies were picked from the solid plate of 5-FU basic salt medium, and verified by colony PCR again, and the transformants with only 1000 bp DNA fragment obtained by PCR amplification were positive clones. The transformant PCR was subjected to sequencing verification and the correct strain was saved, that is, the recombinant engineered strain of *Bacillus subtilis* with the upp gene knocked out, i.e., the recombinant engineered strain of *Bacillus subtilis* without uracil phosphoribosyltransferase activity, named SCK8.

Example 2 Construction of *Bacillus subtilis* Recombinant Strain SCK8-ST1

(1) Construction of Recombinant Integration Vector pSS-amyE-FR

According to the gene sequence of α-amylase coding gene amyG derived from *Bacillus subtilis* 168 (NCBI-ProteinID: NP_388186) in the KEGG database, primers were designed. The upstream 500 bp homologous fragment and the downstream 500 bp homologous fragment of amyG coding gene were amplified by PCR, and constructed into integration vector pSS by simple cloning connection method (You, C., Zhang, X. Z., & Zhang, Y. H. (2012). Simple cloning via direct transformation of PCR product (DNA Multimer) to *Escherichia coli* and *Bacillus subtilis*. Appl. Environ. Microbiol., 78(5), 1593-1595. doi: 10.1128/AEM.07105-11) to obtain a recombinant integration vector pSS-amyE-FR.

(2) Construction of *Bacillus subtilis* Recombinant Strain SCK8-ST1

*Bacillus subtilis* strain SCK8 super competent cells (200 μL) were prepared, and the recombinant integration pSS-amyE-FR (1 μg) was evenly mixed with *Bacillus subtilis* strain SCK8 super competent cells (200 μL), and then placed in a shaker at 37 °C for 90 min to recover. The bacterial solution was coated on solid medium LB (yeast extract 5 g/L, peptone 10 g/L, sodium chloride 10 g/L) containing chloramphenicol (5 μg/mL), and then placed in a 37 °C incubator for 14 to 16 h.

The positive single-crossover transformant colony grown on the chloramphenicol-resistant plate was picked for colony PCR verification, and those with the two bands of 1000 bp DNA fragment and 2000 bp DNA fragment obtained by PCR amplification (where, the size of the 1000 bp DNA fragment was the fragment size of the upstream and downstream homology arms of the amyE coding gene in the vector pSS-amyE-FR, the size of the 2000 bp DNA fragment was the size of the fragment on the genome comprising the upstream homology arm of the amyE conding gene, the amyl conding gene, and the downstream homology arm of the amyE conding gene) were positive clones.

Positive clones were picked and transferred to LB medium without adding antibiotics for 8 to 12 h, then 200 μL of the bacterial solution was centrifuged to remove the supernatant, then resuspended in sterile water and coated on a solid plate of 5-FU basic salt medium (40% glucose 20.0 ml/L, 4% glutamine 50.0 mL/L, 0.5% histidine 10.0 mL/L, 1% vitamin B1 1.0 mL/L, 20 mM 5-FU 500 μL/L, 10×spizizen 100.0 mL/L, 1000×trace elements 1.0 mL/L), and placed in a 37 °C incubator for 24 h. The purpose of this step was to promote the intramolecular homologous recombination of positive transformants by culturing in LB medium without adding antibiotics, and then to obtain amyE knockout target transformants by screening and culturing in 5-FU basic salt medium.

Several colonies were picked from the solid plate of 5-FU basic salt medium, and verified by colony PCR again, and the transformants with only 1000 bp DNA fragment obtained by PCR amplification were positive clones. The transformant PCR was subjected to sequencing verification and the correct strain was saved, that is, the recombinant engineered strain of *Bacillus subtilis* with the amyG gene knocked out, i.e., the recombinant engineered strain of *Bacillus subtilis* without α-amylase activity, named SCK8-ST1.

Example 3 Construction of *Bacillus subtilis* Recombinant Strain SCK8-ST2

(1) Construction of Recombinant Integration Vector pSS-spoIIAC-FR

According to the gene sequence of sporulating RNA polymerase of factor coding gene spoIIAC derived from *Bacillus subtilis* 168 (NCBI-ProteinID: NP_390226) in the KEGG database, primers were designed. The upstream 500 bp homologous fragment and the downstream 500 bp homologous fragment of spoIIAC coding gene were amplified by PCR, and constructed into integration vector pSS by simple cloning connection method (You, C., Zhang, X. Z., & Zhang, Y. H. (2012). Simple cloning via direct transformation of PCR product (DNA Multimer) to *Escherichia coli* and *Bacillus subtilis*. Appl. Environ. Microbiol., 78(5), 1593-1595. doi: 10.1128/AEM.07105-11) to obtain a recombinant integration vector pSS-spoIIAC-FR.

(2) Construction of *Bacillus subtilis* Recombinant Strain SCK8-ST2

*Bacillus subtilis* strain SCK8-ST1 super competent cells (200 μL) were prepared, and the recombinant integration pSS-spoIIAC-FR (1 μg) was evenly mixed with *Bacillus subtilis* strain SCK8-ST1 super competent cells (200 μL), and then placed in a shaker at 37 °C for 90 min to recover. The bacterial solution was coated on solid medium LB (yeast extract 5 g/L, peptone 10 g/L, sodium chloride 10 g/L) containing chloramphenicol (5 μg/mL), and then placed in a 37 °C incubator for 14 to 16 h.

The positive single-crossover transformant colony grown on the chloramphenicol-resistant plate was picked for colony PCR verification, and those with the two bands of 1000 bp DNA fragment and 2000 bp DNA fragment obtained by PCR amplification (where, the size of the 1000 bp DNA fragment was the fragment size of the upstream and downstream homology arms of the spoIIAC coding gene in the vector pSS-spoIIAC-FR, the size of the 2000 bp DNA fragment was the size of the fragment on the genome comprising the upstream homology arm of the spoIIAC conding gene, the spoIIAC conding gene, and the downstream homology arm of the spoIIAC conding gene) were positive clones.

Positive clones were picked and transferred to LB medium without adding antibiotics for 8 to 12 h, then 200 μL of the bacterial solution was centrifuged to remove the supernatant, then resuspended in sterile water and coated on a solid plate of 5-FU basic salt medium (40% glucose 20.0 ml/L, 4% glutamine 50.0 mL/L, 0.5% histidine 10.0 mL/L, 1% vitamin B1 1.0 mL/L, 20 mM 5-FU 500 μL/L, 10×spizizen 100.0 mL/L, 1000×trace elements 1.0 mL/L), and placed in a 37 °C incubator for 24 h. The purpose of this step was to promote the intramolecular homologous recombination of positive transformants by culturing in LB medium without adding antibiotics, and then to obtain spoIIAC knockout target transformants by screening and culturing in 5-FU basic salt medium.

Several colonies were picked from the solid plate of 5-FU basic salt medium, and verified by colony PCR again, and the transformants with only 1000 bp DNA fragment obtained by PCR amplification were positive clones. The transformant PCR was subjected to sequencing verification and the correct strain was saved, that is, the recombinant engineered strain of *Bacillus subtilis* with the sporulating spoIIAC gene knocked out, i.e., the recombinant engineered strain of *Bacillus subtilis* without sporulating RNA polymerase of factor activity, named SCK8-ST2.

Example 4 Construction of *Bacillus subtilis* Recombinant Strain SCK8-ST3

(1) Construction of Recombinant Integration Vector pSS-srfAC-FR

According to the gene sequence of surface-active peptide synthase subunit 3 coding gene srfAC derived from *Bacillus subtilis* 168 (NCBI-ProteinID: NP_388233) in the KEGG database, primers were designed. The upstream 500 bp homologous fragment and the downstream 500 bp homologous fragment of srfAC coding gene were amplified by PCR, and constructed into integration vector pSS by simple cloning connection method (You, C., Zhang, X. Z., & Zhang, Y. H. (2012). Simple cloning via direct transformation of PCR product (DNA Multimer) to *Escherichia coli* and *Bacillus subtilis*. Appl. Environ. Microbiol., 78(5), 1593-1595. doi: 10.1128/AEM.07105-11) to obtain a recombinant integration vector pSS-srfAC-FR.

(2) Construction of *Bacillus subtilis* Recombinant Strain SCK8-ST3

*Bacillus subtilis* strain SCK8-ST2 super competent cells (200 μL) were prepared, and the recombinant integration pSS-srfAC-FR (1 μg) was evenly mixed with *Bacillus subtilis* strain SCK8-ST2 super competent cells (200 μL), and then placed in a shaker at 37 °C for 90 min to recover. The bacterial solution was coated on solid medium LB (yeast extract 5 g/L, peptone 10 g/L, sodium chloride 10 g/L) containing chloramphenicol (5 μg/mL), and then placed in a 37 °C incubator for 14 to 16 h.

The positive single-crossover transformant colony grown on the chloramphenicol-resistant plate was picked for colony PCR verification, and those with the two bands of 1000 bp DNA fragment and 2000 bp DNA fragment obtained by PCR amplification (where, the size of the 1000 bp DNA fragment was the fragment size of the upstream and downstream homology arms of the srfAC coding gene in the vector pSS-srfAC-FR, the size of the 2000 bp DNA fragment was the size of the fragment on the genome comprising the upstream homology arm of the srfAC conding gene, the srfAC conding gene, and the downstream homology arm of the srfAC conding gene) were positive clones.

Positive clones were picked and transferred to LB medium without adding antibiotics for 8 to 12 h, then 200 μL of the bacterial solution was centrifuged to remove the supernatant, then resuspended in sterile water and coated on a solid plate of 5-FU basic salt medium (40% glucose 20.0 ml/L, 4% glutamine 50.0 mL/L, 0.5% histidine 10.0 mL/L, 1% vitamin B1 1.0 mL/L, 20 mM 5-FU 500 μL/L, 10×spizizen 100.0 mL/L, 1000×trace elements 1.0 mL/L), and placed in a 37 °C incubator for 24 h. The purpose of this step was to promote the intramolecular homologous recombination of positive transformants by culturing in LB medium without adding antibiotics, and then to obtain srfAC knockout target transformants by screening and culturing in 5-FU basic salt medium.

Several colonies were picked from the solid plate of 5-FU basic salt medium, and verified by colony PCR again, and the transformants with only 1000 bp DNA fragment obtained by PCR amplification were positive clones. The transformant PCR was subjected to sequencing verification and the correct strain was saved, that is, the recombinant engineered strain of *Bacillus subtilis* with the srfAC gene knocked out, i.e., the recombinant engineered strain of *Bacillus subtilis* without surface-active peptide synthase subunit 3 activity, named SCK8-ST3.

Example 5: Construction of Recombinant Vector (1) Construction of pMA5-Py1b-aGP

The thermalstable α-glucan phosphorylase in the Example is from *Thermococcus kodakarensis*. The thermalstable α-glucan phosphorylase coding gene agp sequence (NCBI-ProteinID: BAD85595) was synthesized and ligated to a common plasmid by Genewiz Suzhou. The agp gene, encoding thermalstable α-glucan phosphorylase, was obtained by PCR using a pair of primers. Using primers 299-F: 5'-AGAAACAACAAAGGGGGAGATTTGTatggtgaacgtttccaatgccgttg-3' (SEQ ID NO: 1) and 300-R: 5'-gcttgagctcgactctagaggatcctcagtcaagtcccttccacttgacca-3' (SEQ ID NO: 2); The pMA5- Py1b linear backbone was obtained by PCR using a pair of primers. Using primers 301-F: 5'-tggtcaagtggaagggacttgactgaggatcctagagagtcgagctcaagc-3' (SEQ ID NO: 3) and 302-R: 5'-caacggcattggaaacgttcaccatACAAATCTCCCCCCCTTTGTTGTTTCT-3' (SEQ ID NO: 4);

All primers were synthesized by Genewiz Suzhou. The PCR conditions for the gene were denaturation at 94 °C for 5 min, 30 cycles according to the following parameters: denaturation at 94 °C for 15 s, annealing at 58 °C for 15 s, extension at 72 °C for 1 min and a final extension at 72 °C for 10 min. The products obtained from the PCR reactions were analysed separately by 0.8% agarose gel electrophoresis of the results. After imaging by gel imaging system to confirm the correct fragment size, the target fragment was recovered by DNA purification and recovery kit (TIANGEN Biotech (Beijing) Co., Ltd., China) for the construction of recombinant expression vector.

Figure 2:
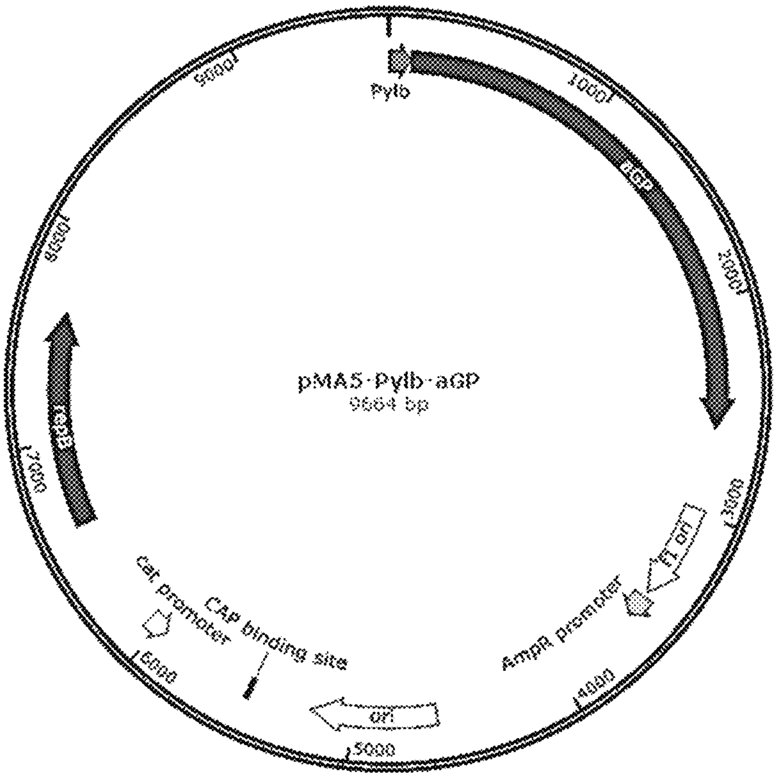
FIG. 2 shows a map of the recombinant expression vector pMA5-Py1b-aGP.

The thermalstable α-glucan phosphorylase gene fragment and the pMA5-Py1b vector backbone were then assembled using POE-PCR. The POE-PCR system was as follows: purified pMA5-Py1b linear backbone, 200 ng; purified thermalstable α-glucan phosphorylase gene fragment, 131 ng; 2× PrimeSTAR MAX DNA Polymerase (TaKaRa Bio (Dalian), China), 25 μL, supplemented with water to 50 μL. The POE-PCR conditions were denaturation at 98 °C for 2 min, 30 cycles according to the following parameters: denaturation at 98 °C for 15 s, annealing at 58 °C for 15 s, extension at 72 °C for 3.5 min and a final extension at 72 °C for 5 min. The ligated product was transformed into competent *E. coli* Top 10 by calcium chloride method, and the transformants were selected for colony PCR and double enzyme digestion identification, and 2-3 positive transformants were selected for further verification by sequencing. The sequencing results showed that the pMA5-Py1b-aGP recombinant co-expression vector was successfully obtained, and the plasmid map is shown in FIG. 2.

(2) Construction of pMA5-Py1b-PGM

The thermostable glucose phosphomutase in the Example is from *Thermococcus kodakarensis*. The thermostable glucose phosphomutase coding gene pgm sequence (NCBI-ProteinID: BAD85297) was synthesized and ligated to a common plasmid by Genewiz Suzhou. The thermostable glucose phosphomutase coding gene pgm was obtained from genomic DNA by PCR using a pair of primers. Using primers 327-F: 5'-AGAAACAACAAAGGGGGAGATTTGTatgggcaaactgtttggtaccttcg-3' (SEQ ID NO: 5) and 328-R: 5'-agcttgagctcgactctagaggatccTTAacctttcagtgcttcttccagc-3' (SEQ ID NO: 6); The pMA5-Py1b linear backbone was obtained by PCR using a pair of primers. Using primers 329-F: 5'-gctggaagaagagcactgaaaggtTAAggatcctctagagagtcgagctcaagct-3' (SEQ ID NO: 7) and 330-R: 5'-cgaaggtaccaaacagtttgcccatACAAATCTCCCCCCCTTTGTTGTTTCT-3' (SEQ ID NO: 8);

All primers were synthesized by Genewiz Suzhou. The PCR conditions for the gene were denaturation at 94 °C for 5 min, 30 cycles according to the following parameters: denaturation at 94 °C for 15 s, annealing at 58 °C for 15 s, extension at 72 °C for 1 min and a final extension at 72 °C for 10 min. The products obtained from the PCR reactions were analysed separately by 0.8% agarose gel electrophoresis of the results. After imaging by gel imaging system to confirm the correct fragment size, the target fragment was recovered by DNA purification and recovery kit (TIANGEN Biotech (Beijing) Co., Ltd., China) for the construction of recombinant expression vector.

Figure 3:
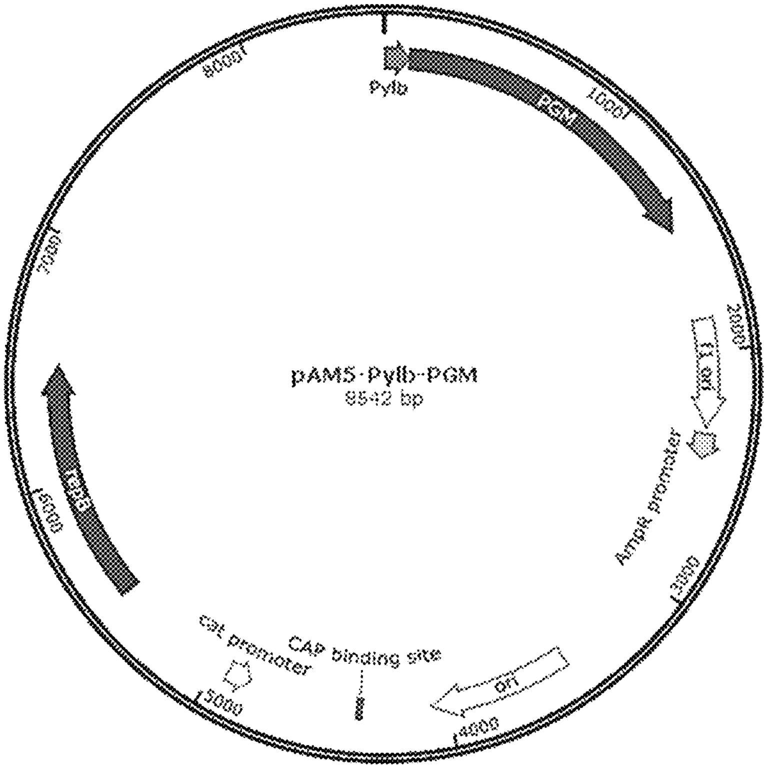
FIG. 3 shows a map of the recombinant expression vector pMA5-Py1b-PGM.

The thermostable glucose phosphomutase gene fragment and the pMA5-Py1b vector backbone were then assembled using POE-PCR. The POE-PCR system was as follows: purified pMA5-Py1b linear backbone, 200 ng; purified thermostable glucose phosphomutase gene fragment, 131 ng; 2× PrimeSTAR MAX DNA Polymerase (TaKaRa Bio (Dalian), China), 25 μL, supplemented with water to 50 μL. The POE-PCR conditions were denaturation at 98 °C for 2 min, 30 cycles according to the following parameters: denaturation at 98 °C for 15 s, annealing at 58 °C for 15 s, extension at 72 °C for 3.5 min and a final extension at 72 °C for 5 min. The ligated product was transformed into competent *E. coli* Top10 by calcium chloride method, and the transformants were selected for colony PCR and double enzyme digestion identification, and 2-3 positive transformants were selected for further verification by sequencing. The sequencing results showed that the pMA5-Py1b-PGM recombinant co-expression vector was successfully obtained, and the plasmid map is shown in FIG. 3.

(3) Construction of pMA5-Py1b-PGI

The thermalstable glucose phosphate isomerase in the Example is from *Thermus thermophilus*. The thermalstable glucose phosphate isomerase coding gene pgi sequence (NCBI-ProteinID: AAS82052) was synthesized and ligated to a common plasmid by Genewiz Suzhou. The thermalstable glucose phosphate isomerase coding gene pgi was obtained from genomic DNA by PCR using a pair of primers. Using primers 331-F: 5'-AGAAACAACAAAGGGGGAGATTTGTATGCTGCGTCTGGATACTCGCTTTC-3' (SEQ ID NO: 9) and 332-R: 5'-agcttgagctcgactctagaggatccTTAACCAGCCAGGCGTTTACGAGTC-3' (SEQ ID NO: 10); The pMA5-Py1b linear backbone was obtained by PCR using a pair of primers. Using primers 333-F: 5'-GACTCGTAAACGCCTGGCTGGTTAAggatcctagagagcttcgagctcaagct-3' (SEQ ID NO: 11) and 334-R: 5'-GAAAGCGAGTATCCAGACGCAGCATACAAATCTCCCCCCCTTTGTTGTTTCT-3' (SEQ ID NO: 16);

All primers were synthesized by Genewiz Suzhou. The PCR conditions for the gene were denaturation at 94 °C for 5 min, 30 cycles according to the following parameters: denaturation at 94 °C for 15 s, annealing at 58 °C for 15 s, extension at 72 °C for 1 min and a final extension at 72 °C for 10 min. The products obtained from the PCR reactions were analysed separately by 0.8% agarose gel electrophoresis of the results. After imaging by gel imaging system to confirm the correct fragment size, the target fragment was recovered by DNA purification and recovery kit (TIANGEN Biotech (Beijing) Co., Ltd., China) for the construction of recombinant expression vector.

Figure 4:
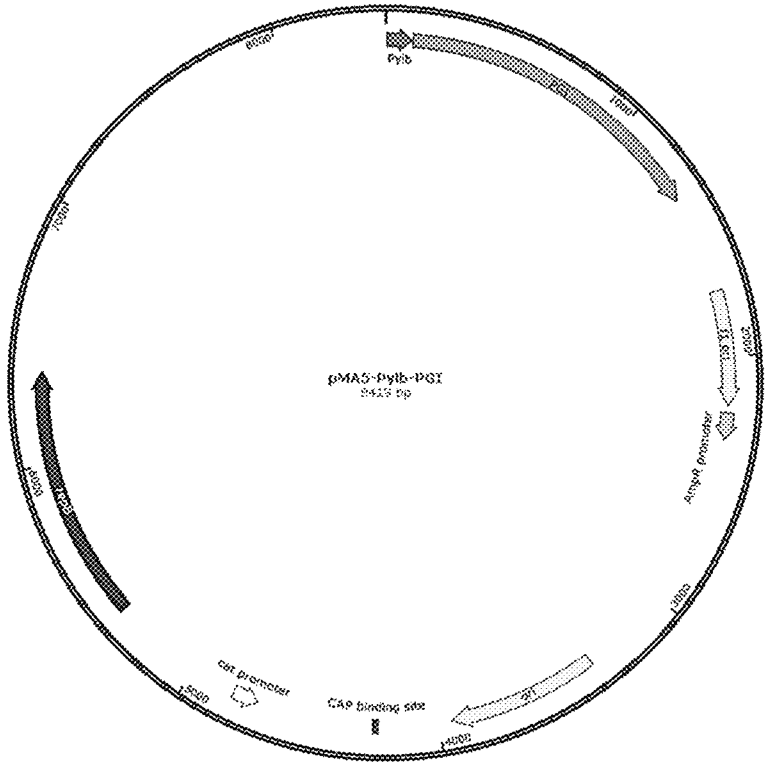
FIG. 4 shows a map of the recombinant expression vector pMA5-Py1b-PGI.

The thermalstable glucose phosphate isomerase gene fragment and the pMA5-Py1b vector backbone were then assembled using POE-PCR. The POE-PCR system was as follows: purified pMA5-Py1b linear backbone, 200 ng; purified thermalstable glucose phosphate isomerase gene fragment, 131 ng; 2× PrimeSTAR MAX DNA Polymerase (TaKaRa Bio (Dalian), China), 25 μL, supplemented with water to 50 μL. The POE-PCR conditions were denaturation at 98 °C for 2 min, 30 cycles according to the following parameters: denaturation at 98 °C for 15 s, annealing at 58 °C for 15 s, extension at 72 °C for 3.5 min and a final extension at 72 °C for 5 min. The ligated product was transformed into competent *E. coli* Top 10 by calcium chloride method, and the transformants were selected for colony PCR and double enzyme digestion identification, and 2-3 positive transformants were selected for further verification by sequencing. The sequencing results showed that the pMA5-Py1b-PGI recombinant co-expression vector was successfully obtained, and the plasmid map is shown in FIG. 4.

(4) Construction of pMA5-Py1b-TPE

The thermalstable 6-tagatose phosphate epimerase in the Example is from *Thermoanaerobacter indiensis*. The thermalstable 6-tagatose phosphate epimerase coding gene tpe sequence (NCBI-ProteinID: B044_RS0101530) was synthesized and ligated to a common plasmid by Genewiz Suzhou. The thermalstable 6-tagatose phosphate epimerase coding gene tpe was obtained from genomic DNA by PCR using a pair of primers. Using primers 335-F: 5'-AGAAACAACAAAGGGGGAGATTTGTatgaaagtttggctggttggtgcct-3' (SEQ ID NO: 12) and 324-R: 5'-agcttgagctcgactctagaggatccTTAtttcaggttgctataccattct-3' (SEQ ID NO: 13); The pMA5-Py1b linear backbone was obtained by PCR using a pair of primers. Using primers 325-F: 5'-agaatggtatagcaacctgaaaTAAggatcctagagagtcgagctcaagct-3' (SEQ ID NO: 14) and 326-R: 5'-aggcaccaaccagccaaactttcatACAAATCTCCCCCCCTTTGTTGTTTCT-3' (SEQ ID NO: 15);

All primers were synthesized by Genewiz Suzhou. The PCR conditions for the gene were denaturation at 94 °C for 5 min, 30 cycles according to the following parameters: denaturation at 94 °C for 15 s, annealing at 58 °C for 15 s, extension at 72 °C for 1 min and a final extension at 72 °C for 10 min. The products obtained from the PCR reactions were analysed separately by 0.8% agarose gel electrophoresis of the results. After imaging by gel imaging system to confirm the correct fragment size, the target fragment was recovered by DNA purification and recovery kit (TIANGEN Biotech (Beijing) Co., Ltd., China) for the construction of recombinant expression vector.

Figure 5:
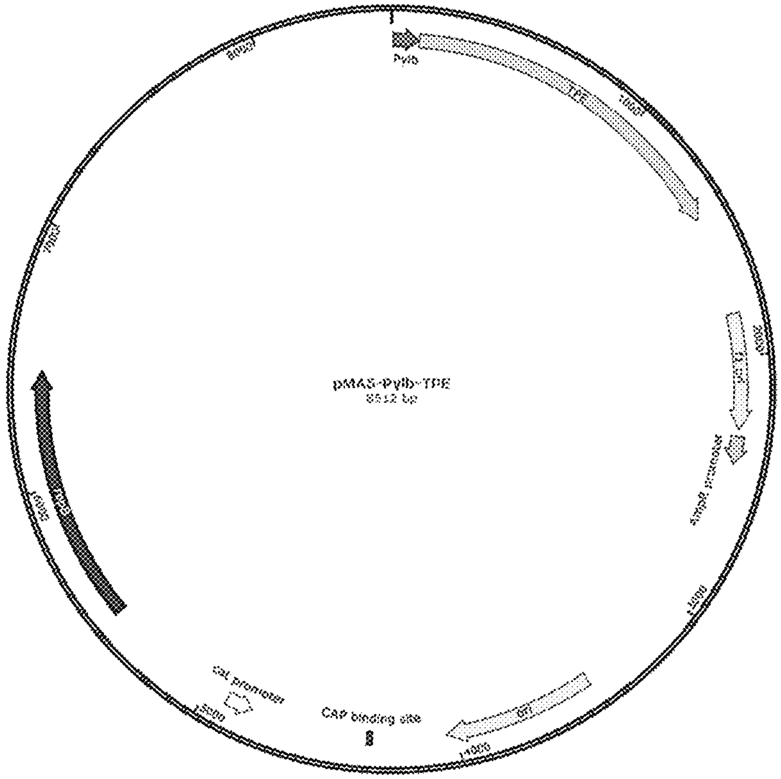
FIG. 5 shows a map of the recombinant expression vector pMA5-Py1b-TPE.

The thermostable 6-tagatose phosphate epimerase gene fragment and the pMA5-Py1b vector backbone were then assembled using POE-PCR. The POE-PCR system was as follows: purified pMA5-Py1b linear backbone, 200 ng;

purified thermostable 6-tagatose phosphate epimerase gene fragment, 131 ng; 2× PrimeSTAR MAX DNA Polymerase (TaKaRa Bio (Dalian), China), 25 μL, supplemented with water to 50 μL. The POE-PCR conditions were denaturation at 98 °C for 2 min, 30 cycles according to the following parameters: denaturation at 98 °C for 15 s, annealing at 58 °C for 15 s, extension at 72 °C for 3.5 min and a final extension at 72 °C for 5 min. The ligated product was transformed into competent *E. coli* Top 10 by calcium chloride method, and the transformants were selected for colony PCR and double enzyme digestion identification, and 2-3 positive transformants were selected for further verification by sequencing. The sequencing results showed that the pMA5-Py1b-TPE recombinant co-expression vector was successfully obtained, and the plasmid map is shown in FIG. 5.

(5) Construction of pMA5-Py1b-TPP

The thermalstable 6-tagatose phosphate phosphatase in the Example is from *Archaeoglobus fulgidus*. The thermalstable 6-tagatose phosphate phosphatase coding gene tpp sequence (NCBI-ProteinID: AAB90791) was synthesized and ligated to a common plasmid by Genewiz Suzhou. The thermalstable 6-tagatose phosphate phosphatase coding gene tpp was obtained from genomic DNA by PCR using a pair of primers. Using primers 339-F: 5'-AGAAACAACAAAGGGGGAGATTTGTATGTT-CAAGCCGAAAGCGATCGCGG-3' (SEQ ID NO: 17) and 340-R: 5'-agcttgagctcgactctagaggatccT-TAACGCAGCAGGCCCAGAAACTG-3' (SEQ ID NO: 18); The pMA5-Py1b linear backbone was obtained by PCR using a pair of primers. Using primers 341-F: 5'-CAGTTTCTGGGCCTGCTGCGT-TAAggatcctagagagagtcgagctcaagct-3' (SEQ ID NO: 19) and 342-R: 5'-CCGCGATCGCTTTCGGCTTGAACATA-CAAATCTCCCCCTTTGTTGTTTCT-3' (SEQ ID NO: 20).

All primers were synthesized by Genewiz Suzhou. The PCR conditions for the gene were denaturation at 94 °C for 5 min, 30 cycles according to the following parameters: denaturation at 94 °C for 15 s, annealing at 58 °C for 15 s, extension at 72 °C for 1 min and a final extension at 72 °C for 10 min. The products obtained from the PCR reactions were analysed separately by 0.8% agarose gel electrophoresis of the results. After imaging by gel imaging system to confirm the correct fragment size, the target fragment was recovered by DNA purification and recovery kit (TIANGEN Biotech (Beijing) Co., Ltd., China) for the construction of recombinant expression vector.

Figure 6:
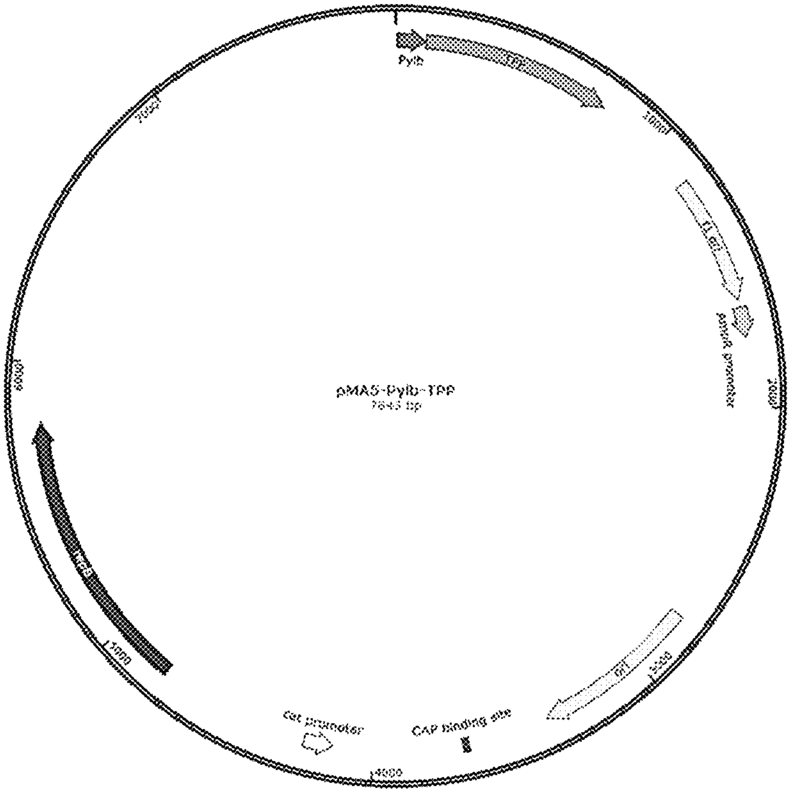
FIG. 6 shows a map of the recombinant expression vector pMA5-Py1b-TPP.

The thermostable 6-tagatose phosphate phosphatase gene fragment and the pMA5-Py1b vector backbone were then assembled using POE-PCR. The POE-PCR system was as follows: purified pMA5-Py1b linear backbone, 200 ng; purified thermostable 6-tagatose phosphate phosphatase gene fragment, 131 ng; 2× PrimeSTAR MAX DNA Polymerase (TaKaRa Bio (Dalian), China), 25 μL, supplemented with water to 50 μL. The POE-PCR conditions were denaturation at 98 °C for 2 min, 30 cycles according to the following parameters: denaturation at 98 °C for 15 s, annealing at 58 °C for 15 s, extension at 72 °C for 3.5 min and a final extension at 72 °C for 5 min. The ligated product was transformed into competent *E. coli* Top 10 by calcium chloride method, and the transformants were selected for colony PCR and double enzyme digestion identification, and 2-3 positive transformants were selected for further verification by sequencing. The sequencing results showed that the pMA5-Py1b-TPP recombinant co-expression vector was successfully obtained, and the plasmid map is shown in FIG. 6.

(6) Construction of pMA5-Py1b-aGP-PGM-PGI-TPE-TPP

In the example the thermostable α-glucan phosphorylase is from *Thermococcus kodakarensis*; the thermostable glucose phosphomutase is from *Thermococcus kodakarensis*; the thermostable glucose phosphate isomerase is from *Thermus thermophilus*; the thermostable 6-tagatose phosphate epimerase is from *Thermoanaerobacter indiensis*; and the thermostable 6-tagatose phosphate phosphatase is from *Archaeoglobus fulgidus*. The thermostable α-glucan phosphorylase coding gene agp (NCBI-ProteinID: BAD85595) was obtained by PCR using primers 350-F: 5'-AGAAACAACAAAGGGGGAGTTGTatggtgaacgtttc-caatgccgttg-3' (SEQ ID NO: 21) and 351-R: 5'-cgaaggtac-caaacagtttgcccatTTTGAATTCCTCCTTTtcagtcaagtcccttc-cacttgacc-3'; The thermostable glucose phosphomutase coding gene pgm (NCBI-ProteinID: BAD85297) was obtained by PCR using primers 352-F: 5'-ggtcaagtg-gaagggacttgactgaAAAGGAGGAATT-CAAAatgggcaaactgtttggtaccttcg-3' (SEQ ID NO: 22) and 353-R: 5'-GAAAGCGAGTATCCAGACGCAGCATTTT-GAATTCCTCCTTTTTAacctttcagtgcttcttccagc-3' (SEQ ID NO: 24); The thermostable glucose phosphate isomerase coding gene pgi (NCBI-ProteinID: AAS82052) was obtained by PCR using primers 354-F: 5'-gctggaagaagcact-gaaaggtTAAAAAGGAGGAATT-CAAAATGCTGCGTCTGGATACTCGCTT TC-3' (SEQ ID NO: 25) and 355-R: 5'-TTTTCAGCG-GATGTTCGGTGTTCATTTTGAATTCCTCCTTTT-CAACCAGCCAGGCGTT TACGAGTC-3' (SEQ ID NO: 26); The thermostable 6-tagatose phosphate epimerase coding gene tpe (NCBI-ProteinID: B044_RS0101530) was obtained by PCR using primers 356-F: 5'-GACTCGTAAACGCCTGGCTGGTTGAAAAGGAG-GAATTCAAAATGAACACCGAACAT CCGCTGAAAA-3' (SEQ ID NO: 27) and 357-R: 5'-ACCGC-GATCGCTTTCGGCTTGAACATTTTGAATTCCTCC-TTTttaAATCAGTTTGAATTC ACCGCTG-3' (SEQ ID NO: 28); The thermostable 6-tagatose phosphate phosphatase coding gene tpp (NCBI-ProteinID: AAB90791) was obtained by PCR using primers 358-F: 5'-CAGCGGT-GAATTCAAACTGATTtaaAAAGGAGGAATT-CAAAATGTTCAAGCCGAAAG CGATCGCGGT-3' (SEQ ID NO: 29) and 359-R: 5'-gcttgagctcgactctagag-gatccTTAACGCAGCAGGCCCAGAAACTGCA-3' (SEQ ID NO: 30); The pMA5-Py1b linear backbone was obtained by PCR using the primers; 360-F: 5'-TGCAGTTTCTGGGCCTGCTGCGT-TAAggatcctagagagtcgagctcaagc-3' (SEQ ID NO: 31) and 361-R: 5'-caacggcattggaaacgttcaccatA-CAAATCTCCCCCTTTGTTGTTTCT-3' (SEQ ID NO: 32).

All primers were synthesized by Genewiz Suzhou. The PCR conditions for the gene were denaturation at 94 °C for 5 min, 30 cycles according to the following parameters: denaturation at 94 °C for 15 s, annealing at 58 °C for 15 s, extension at 72 °C for 1 min and a final extension at 72 °C for 10 min. The products obtained from the PCR reactions were analysed separately by 0.8% agarose gel electrophoresis of the results. After imaging by gel imaging system to confirm the correct fragment size, the target fragment was recovered by DNA purification and recovery kit (TIANGEN Biotech (Beijing) Co., Ltd., China) for the construction of recombinant expression vector.

Figure 7:
FIG. 7 shows a map of the recombinant expression vector pMA5-Py1b-aGP-PGM-PGI-TPE-TPP.

The thermalstable α-glucan phosphorylase gene fragment, the thermalstable glucose phosphomutase gene fragment, the thermalstable glucose phosphate isomerase gene fragment, the thermalstable 6-tagatose phosphate epimerase gene fragment, the thermalstable 6-tagatose phosphate phosphatase gene fragment, and the pMA5-Py1b vector backbone were then assembled using POE-PCR. The POE-PCR system was as follows: purified pMA5-Py1b linear backbone, 200 ng; purified thermalstable α-glucan phosphorylase gene fragment, 131 ng; purified thermalstable glucose phosphomutase gene fragment, 131 ng; purified thermalstable glucose phosphate isomerase gene fragment, 131 ng; purified thermalstable 6-tagatose phosphate epimerase gene fragment, 131 ng; purified thermalstable 6-tagatose phosphate phosphatase gene fragment, 131 ng; 2× PrimeSTAR MAX DNA Polymerase (TaKaRa Bio (Dalian), China), 25 μL, supplemented with water to 50 μL. The POE-PCR conditions were denaturation at 98 °C for 2 min, 30 cycles according to the following parameters: denaturation at 98 °C for 15 s, annealing at 58 °C for 15 s, extension at 72 °C for 3.5 min and a final extension at 72 °C for 5 min. The ligated product was transformed into competent *E. coli* Top 10 by calcium chloride method, and the transformants were selected for colony PCR and double enzyme digestion identification, and 2-3 positive transformants were selected for further verification by sequencing. The sequencing results showed that the pMA5-Py1b-aGP-PGM-PGI-TPE-TPP recombinant co-expression vector was successfully obtained, and the plasmid map is shown in FIG. 7.

Example 6 Construction of Recombinant Engineered Bacteria

The constructed recombinant expression vectors pMA5-Py1b-aGP, pMA5-Py1b-PGM, pMA5-Py1b-PGI, pMA5-Py1b-TPE, pMA5-Py1b-TPP, and pMA5-Py1b-aGP-PGM-PGI-TPE-TPP were separately transformed into *Bacillus subtilis* engineering bacterium SCK8-ST3, incubated overnight in LB test tubes, and the plasmids were extracted by the Plasmid Extraction Kit, and the correct clones SCK8-ST3/pMA5-Py1b-aGP, SCK8-ST3/pMA5-Py1b-PGM, SCK8-ST3/pMA5-Py1b-PGI, SCK8-ST3/pMA5-Py1b-TPE, SCK8-ST3/pMA5-Py1b-TPP and SCK8-ST3/pMA5-Py1b-aGP-PGM-PGI-TPE-TPP were stored.

Example 7 Preparation of Whole Cells of Recombinantly Engineered Bacteria

Recombinant engineered bacteria SCK8-ST3/pMA5-Py1b-aGP, SCK8-ST3/pMA5-Py1b-PGM, SCK8-ST3/pMA5-Py1b-PGI, SCK8-ST3/pMA5-Py1b-TPE, SCK8-ST3/pMA5-Py1b-TPP and SCK8-ST3/pMA5-Py1b-aGP-PGM-PGI-TPE-TPP were respectively picked and inoculated in LB medium containing chlortetracycline and incubated overnight at 37 °C with shaking. Cultures were transferred at 1% inoculum to fresh LB medium containing chimaericin, incubated overnight at 37 °C with shaking, centrifuged at 5500 rpm for 10 min and the supernatant discarded to obtain whole cells expressing thermalstable α-glucan phosphorylase, whole cells expressing thermalstable glucose phosphomutase, whole cells expressing thermalstable glucose phosphate isomerase, whole cells expressing thermalstable 6-tagatose phosphate epimerase, whole cells expressing thermalstable 6-tagatose phosphate phosphatase, and whole cells co-expressing thermalstable α-glucan phosphorylase, thermalstable glucose phosphomutase, thermalstable glucose phosphate isomerase, thermalstable 6-tagatose phosphate epimerase, and thermalstable 6-tagatose phosphate phosphatase.

Example 8 Preparation of Tagatose by Co-Expression of Whole Cell to Catalyze Starch The whole cells co-expressing thermalstable α-glucan phosphorylase, thermalstable glucose phosphomutase, thermalstable glucose phosphate isomerase, thermalstable 6-tagatose phosphate epimerase, and thermalstable 6-tagatose phosphate phosphatase prepared in Example 7 were washed once with 50 mM Tris-HCl buffer (pH 7.5), centrifuged at 5500 rpm for 10 min, the supernatant was discarded, 50 mM Tris-HCl (pH 7.5) buffer was added to the precipitate and the bacteria were resuspended to make $OD_{600}$=about 300. The resuspended bacteria were heat treated at 75 °C for 90 min.

To a 1 L reaction system, a final concentration of 100 g/L starch, 50 mM sodium phosphate buffer (pH 7.5) and heat-treated whole cells were added to make $OD_{600}$=about 20. The reaction was carried out in a water bath shaker at 70 °C for 46 h and samples were taken for high performance liquid chromatography (HPLC) analysis. The HPLC conditions were as follows: the column was Bio-Rad HPX-87H; the flow rate was 0.6 mL/min; the column temperature was 60 °C; the detector was a differential refractive index detector; and the injection volume was 20 μL.

Figure 8:
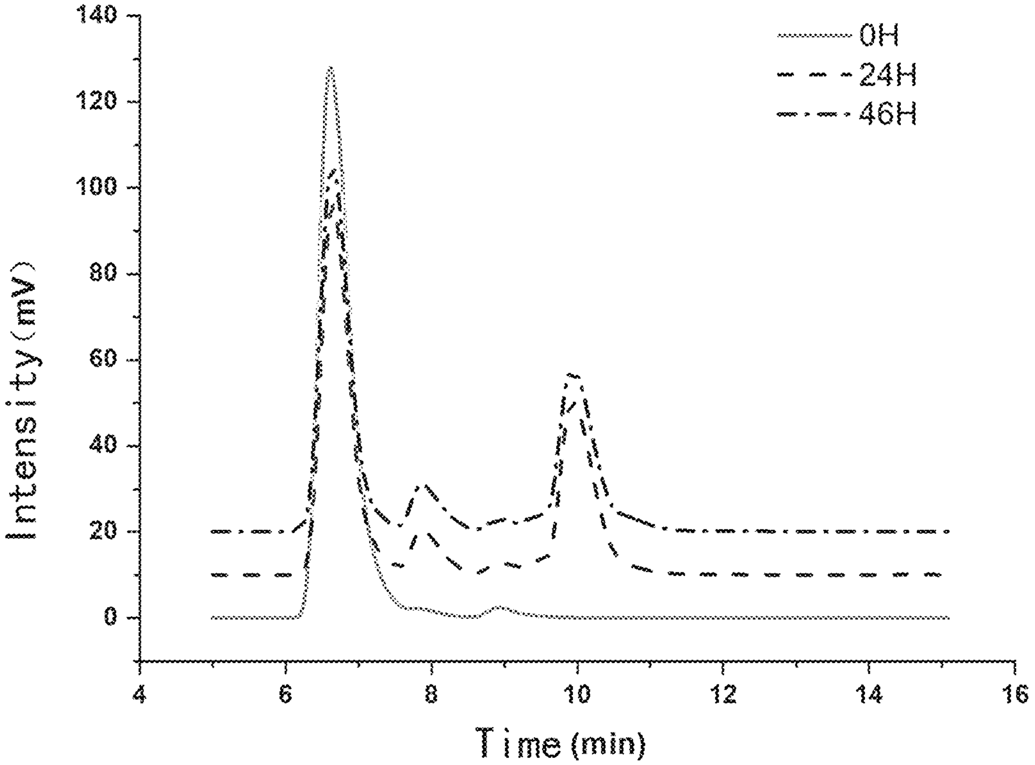
FIG. 8 shows the profile of the yield of tagatose with the reaction time.

In total, three parallel replicate tests were carried out and FIG. 8 shows a graph of the course of the tagatose yield with reaction time. After 46 h of reaction in a water bath shaker at 70 °C, the HPLC test results showed that the tagatose yield reached 50 g/L with a yield of up to 50%.

Example 9 Preparation of Tagatose by Using Whole Cell Mixture to Catalyze Starch The whole cells expressing thermalstable α-glucan phosphorylase, whole cells expressing thermalstable glucose phosphomutase, whole cells expressing thermalstable glucose phosphate isomerase, whole cells expressing thermalstable 6-tagatose phosphate epimerase, whole cells expressing thermalstable 6-tagatose phosphate phosphatase prepared in Example 7 were separately washed once with 50 mM Tris-HCl buffer (pH 7.5), centrifuged at 5500 rpm for 10 min, the supernatant was discarded, 50 mM Tris-HCl (pH 7.5) buffer was respectively added to the precipitates and the bacteria were resuspended to about $OD_{600}$=300. The resuspended bacteria were heat treated at 75 °C for 90 min.

To a 1 L reaction system, a final concentration of 100 g/L starch, 50 mM sodium phosphate buffer (pH 7.5) and the above four heat-treated whole cells were added to make $OD_{600}$=about 20. The whole cells expressing thermalstable α-glucan phosphorylase, whole cells expressing thermalstable glucose phosphomutase, whole cells expressing thermalstable glucose phosphate isomerase, whole cells expressing thermalstable 6-tagatose phosphate epimerase, whole cells expressing thermalstable 6-tagatose phosphate phosphatase were added in a 1:1:1:1:1 ratio. The reaction was carried out in a water bath shaker at 70 °C for 46 h and samples were taken for HPLC analysis. In total, three parallel replicate tests were carried out and the HPLC conditions were the same as in Example 8. After 46 h of reaction in a water bath shaker at 70 °C, the HPLC test results showed that the yield of tagatose reached 73 g/L with a yield of 73%.

Example 10 Production of Tagatose by Using Immobilized Whole Cell to Catalyze Starch Permeable whole cells co-expressing thermalstable α-glucan phosphorylase, thermalstable glucose phosphomutase, thermalstable glucose phosphate isomerase, thermalstable 6-tagatose phosphate epimerase, and thermalstable 6-tagatose phosphate phosphatase were resuspeded with 1 L sodium phosphate buffer (pH 7.0) to make $OD_{600}$=about 400, 1 g montmorillonite was added and mix well. 40 mL of 5% (w/v) aqueous polyethyleneimine was added and flocculated at room temperature, and 20 mL of 50% aqueous glutaraldehyde was added and crosslinked at room temperature for 3 h. Then, the filter cake layer was obtained by suction filtration, and the filter cake was washed with deionized water, extruded to prepare pellets, and dried to obtain immobilized whole cells.

Figure 9:
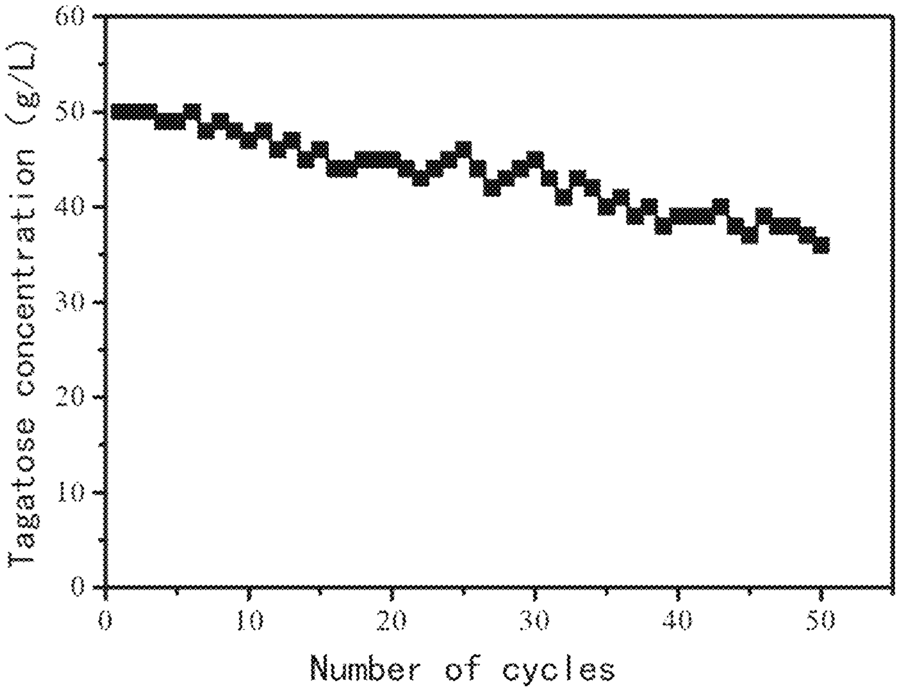
FIG. 9 shows the trend of tagatose production by immobilized co-expressing engineered strain.

To a 1 L reaction system, a final concentration of 100 g/L starch, 50 mM sodium phosphate buffer (pH 7.5) and immobilized whole cells were added to make $OD_{600}$=about 20 and the reaction was carried out in a water bath shaker at 70 °C for 46 h. At the end of the reaction the reaction solution was centrifuged at 4 °C and subjected to high performance liquid chromatography (HPLC) to analyse the tagatose content; the immobilized pellets were collected and washed in buffer for the next batch of reaction. The experimental results are shown in FIG. 9. The results showed that in the production process of tagatose by using immobilized whole cells to continuously catalyze starch, the initial product yield was up to 50%, which decreases with increasing batches of the continuous catalytic reaction and remains around 36% after 50 consecutive batches.

Example 11 Production of Tagatose by Using Immobilized Whole Cell Mixture to Catalyze Starch The permeable whole cells expressing thermalstable α-glucan phosphorylase, permeable whole cells expressing thermalstable glucose phosphomutase, permeable whole cells expressing thermalstable glucose phosphate isomerase, permeable whole cells expressing thermalstable 6-tagatose phosphate epimerase, permeable whole cells expressing thermalstable 6-tagatose phosphate phosphatase in a ratio of 1:1:1:1:1 were resuspended with 1 L of sodium phosphate buffer (pH 7.0) to make $OD_{600}$=about 300, 0.8 g of montmorillonite was added and mixed well. 35 mL of 5% (w/v) aqueous polyethyleneimine was added and flocculated at room temperature, and 18 mL of 50% aqueous glutaraldehyde was added and crosslinked at room temperature for 3 h. Then, the filter cake layer was obtained by suction filtration, and the filter cake was washed with deionized water, extruded to prepare pellets, and dried to obtain immobilized whole cell mixture.

Figure 10:
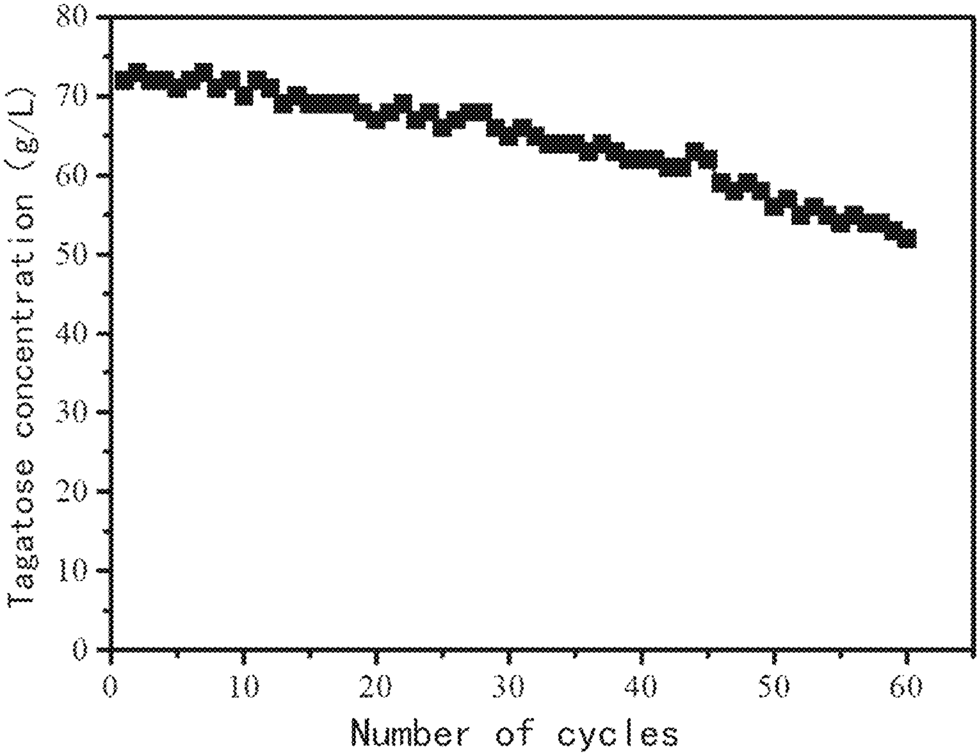
FIG. 10 shows the trend of tagatose production by immobilization of separately expressing engineered strains.

To a 1 L reaction system, a final concentration of 100 g/L starch, 50 mM sodium phosphate buffer (pH 7.5) and immobilized whole cells were added to make $OD_{600}$=about 20 and the reaction was carried out in a water bath shaker at 70 °C for 46 h. At the end of the reaction the reaction solution was centrifuged at 4 °C and subjected to high performance liquid chromatography (HPLC) to analyse the tagatose content; the immobilized pellets were collected and washed in buffer for the next batch of reaction. The experimental results are shown in FIG. 10. The results showed that the product yields were greater than 50% and up to 73% in 60 consecutive batches of catalysis. The experimental results are shown in FIG. 10. The results showed that during the reaction continuously catalyzed by the immobilized whole cells, the initial product yield was up to 73%, which decreases with increasing batches of the continuous catalytic reaction and remains around 52% after 60 consecutive batches.

The invention claimed is:

1. A *Bacillus subtilis* genetically engineered bacterium for producing tagatose, characterized in that said genetically engineered bacterium is a *Bacillus subtilis* genetically engineered bacterium co-expressing an α-glucan phosphorylase gene from *Thermococcus kodakarensis*, a glucose phosphomutase gene from *Thermococcus kodakarensis*, a glucose phosphate isomerase gene from *Thermus thermophilus*, a 6-tagatose phosphate epimerase gene from *Thermoanaerobacter indiensis*, and a 6-tagatose phosphate phosphatase gene from *Archaeoglobus fulgidus*, or a mixture of *Bacillus subtilis* genetically engineered bacteria respectively expressing an α-glucan phosphorylase gene from *Thermococcus kodakarensis*, a glucose phosphomutase gene from *Thermococcus kodakarensis*, a glucose phosphate isomerase gene from *Thermus thermophilus*, a 6-tagatose phosphate epimerase gene from *Thermoanaerobacter indiensis, and a* 6-tagatose phosphate phosphatase gene from *Archaeoglobus fulgidus.*

2. The genetically engineered bacterium according to claim 1, characterized in that a starting strain of said *Bacillus subtilis* is a protease-knockout strain of *Bacillus subtilis* strain.

3. The genetically engineered bacterium according to claim 1, characterized in that said α-glucan phosphorylase, glucose phosphomutase, glucose phosphate isomerase, 6-tagatose phosphate epimerase, and 6-tagatose phosphate phosphatase are respectively thermostable α-glucan phosphorylase, thermostable glucose phosphomutase, thermostable glucose phosphate isomerase, thermostable 6-tagatose phosphate epimerase, and thermostable 6-tagatose phosphate phosphatase, and wherein being thermostable refers to having enzyme activity above 40 °C.

4. The genetically engineered bacterium according to claim 1, characterized in that endogenous uracil phosphoribosyltransferase gene, α-amylase gene, sporulating RNA polymerase $\sigma^F$ factor gene, and surface-active peptide synthase subunit 3 gene are all inactivated or knocked out in said genetically engineered bacterium.

5. An expression vector, characterized in that it comprises an α-glucan phosphorylase gene from *Thermococcus kodakarensis*, a glucose phosphomutase gene from *Thermococcus kodakarensis*, a glucose phosphate isomerase gene from *Thermus thermophilus*, a 6-tagatose phosphate epimerase gene from *Thermoanaerobacter indiensis*, and a 6-tagatose phosphate phosphatase gene from *Archaeoglobus fulgidus* and is capable of co-expressing these genes.

6. A method for producing tagatose by utilizing a whole cell of the genetically engineered bacterium according to claim 1 to catalyze starch, comprising the steps of (1) fermenting said *Bacillus subtilis* genetically engineered bacterium to obtain whole cells;

(2) subjecting the whole cells of Bacillus subtilis obtained in step (1) to a cell membrane permeability treatment to obtain permeable whole cells;

(3) catalyzing starch by utilizing the permeable whole cells obtained in step (2) to produce tagatose, wherein for co-expressing whole cells of *Bacillus subtilis* engineered bacterium, the whole cells are used directly for catalysis, and for whole cells of *Bacillus subtilis* engineered bacterium expressing various enzymes separately, the whole cells are mixed for catalysis.

7. The method according to claim 6, characterized in further comprising immobilizing the *Bacillus subtilis* permeable whole cells obtained in step (2) to obtain immobilized whole cells, or a mixture of immobilized whole cells, which can then be used for catalysis.

8. The method according to claim 6, characterized in that the preparation of whole cells of said step (1) is obtained by means of a fermentation method suitable for expression of exogenous protein.

9. The method according to claim 6, characterized in that the cell membrane permeability treatment of said step (2) is obtained by heat treatment, addition of organic solvents or addition of surfactant treatment.

10. The method according to claim 9, characterized in that said organic solvent is selected from acetone, acetonitrile; said surfactant is selected from cetyl trimethyl ammonium bromide, Tween-80.

11. The method according to claim 9, characterized in that said heat treatment is carried out at a temperature of 45 to 100 °C and a heat treatment time of 10 to 100 min; and cell concentration at the time of treatment is $OD_{600}$=10 to 300.

12. The method according to claim 11, characterized in that said heat treatment is carried out at a temperature of 70 to 80 °C and a heat treatment time of 50 to 70 min; and cell concentration at the time of treatment is $OD_{600}$=30 to 150.

13. The method according to claim 9, characterized in that said heat treatment is carried out in a buffer selected from HEPES buffer, phosphate buffer, Tris buffer, and acetate buffer.

14. The method according to claim 6, characterized in that concentration of the substrate starch in the reaction system catalyzed in step (3) is 50 to 300 g/L; reaction conditions are: 0.5 to 96 h at pH 5.0 to 8.0 and 40 to 80 °C.

15. The method according to claim 14, characterized in that concentration of the substrate starch in the reaction system catalyzed in step (3) is 100 to 200 g/L; reaction conditions are: 12 to 60 h at pH 6.5 to 7.5 and 45 to 75 °C.

16. The method according to claim 6, characterized in that the reaction catalyzed in said step (3) is carried out in a buffer selected from HEPES buffer, phosphate buffer, Tris buffer, and acetate buffer.

17. The method according to claim 6, characterized in that for *Bacillus subtilis* engineered bacterium permeable whole cells expressing various enzymes separately, the mixture is made by mixing permeable whole cells expressing α-glucan phosphorylase, permeable whole cells expressing glucose phosphomutase, permeable whole cells expressing glucose phosphate isomerase, permeable whole cells expressing 6-tagatose phosphate epimerase, and permeable whole cells expressing 6-tagatose phosphate phosphatase in a ratio of (0.1-10):(0.1-10):(0.1-10):(0.1-10):(0.1-10).

18. The method according to claim 6, characterized in that said permeable whole cells are immobilized by resuspending said permeable whole cells with sodium phosphate or potassium phosphate buffer, adding inorganic clay and stirring well; subsequently adding polyethyleneimine aqueous solution for flocculation, then adding cross-linking agent for cross-linking; then filtering to obtain a filter cake layer which is washed with deionized water and squeezed to prepare into pellets, dried to obtain the immobilized whole cells.

19. The method according to claim 18, characterized in that said inorganic clay is selected from montmorillonite, diatomaceous earth, kaolin and bentonite; said crosslinker is selected from glutaraldehyde, trihydroxymethylphosphine, N,N-methylenebisacrylamide, epichlorohydrin and genipin.

* * * * *

SEQUENCE LISTING

```
<160> NUMBER OF SEQ ID NOS: 32

<210> SEQ ID NO 1
<211> LENGTH: 50
<212> TYPE: DNA
<213> ORGANISM: Artificial Sequence
<220> FEATURE:
<223> OTHER INFORMATION: Primer

<400> SEQUENCE: 1

agaaacaaca aagggggaga tttgtatggt gaacgtttcc aatgccgttg              50


<210> SEQ ID NO 2
<211> LENGTH: 51
<212> TYPE: DNA
<213> ORGANISM: Artificial Sequence
<220> FEATURE:
<223> OTHER INFORMATION: Primer

<400> SEQUENCE: 2

gcttgagctc gactctagag gatcctcagt caagtccctt ccacttgacc a            51


<210> SEQ ID NO 3
<211> LENGTH: 51
<212> TYPE: DNA
<213> ORGANISM: Artificial Sequence
<220> FEATURE:
<223> OTHER INFORMATION: Primer

<400> SEQUENCE: 3

tggtcaagtg gaagggactt gactgaggat cctctagagt cgagctcaag c            51
```

<210> SEQ ID NO 4
<211> LENGTH: 50
<212> TYPE: DNA
<213> ORGANISM: Artificial Sequence
<220> FEATURE:
<223> OTHER INFORMATION: Primer

<400> SEQUENCE: 4
caacggcatt ggaaacgttc accatacaaa tctccccctt tgttgtttct 50

<210> SEQ ID NO 5
<211> LENGTH: 50
<212> TYPE: DNA
<213> ORGANISM: Artificial Sequence
<220> FEATURE:
<223> OTHER INFORMATION: Primer

<400> SEQUENCE: 5
agaaacaaca aagggggaga tttgtatggg caaactgttt ggtaccttcg 50

<210> SEQ ID NO 6
<211> LENGTH: 51
<212> TYPE: DNA
<213> ORGANISM: Artificial Sequence
<220> FEATURE:
<223> OTHER INFORMATION: Primer

<400> SEQUENCE: 6
agcttgagct cgactctaga ggatccttaa cctttcagtg cttcttccag c 51

<210> SEQ ID NO 7
<211> LENGTH: 51
<212> TYPE: DNA
<213> ORGANISM: Artificial Sequence
<220> FEATURE:
<223> OTHER INFORMATION: Primer

<400> SEQUENCE: 7
gctggaagaa gcactgaaag gttaaggatc ctctagagtc gagctcaagc t 51

<210> SEQ ID NO 8
<211> LENGTH: 50
<212> TYPE: DNA
<213> ORGANISM: Artificial Sequence
<220> FEATURE:
<223> OTHER INFORMATION: Primer

<400> SEQUENCE: 8
cgaaggtacc aaacagtttg cccatacaaa tctccccctt tgttgtttct 50

<210> SEQ ID NO 9
<211> LENGTH: 50
<212> TYPE: DNA
<213> ORGANISM: Artificial Sequence
<220> FEATURE:
<223> OTHER INFORMATION: Primer

<400> SEQUENCE: 9
agaaacaaca aagggggaga tttgtatgct gcgtctggat actcgctttc 50

<210> SEQ ID NO 10
<211> LENGTH: 51
<212> TYPE: DNA
<213> ORGANISM: Artificial Sequence
<220> FEATURE:
<223> OTHER INFORMATION: Primer

<400> SEQUENCE: 10
agcttgagct cgactctaga ggatccttaa ccagccaggc gtttacgagt c 51

<210> SEQ ID NO 11
<211> LENGTH: 51
<212> TYPE: DNA
<213> ORGANISM: Artificial Sequence
<220> FEATURE:
<223> OTHER INFORMATION: Primer

<400> SEQUENCE: 11
gactcgtaaa cgcctggctg gttaaggatc ctctagagtc gagctcaagc t 51

<210> SEQ ID NO 12
<211> LENGTH: 50
<212> TYPE: DNA
<213> ORGANISM: Artificial Sequence
<220> FEATURE:
<223> OTHER INFORMATION: Primer

<400> SEQUENCE: 12
agaaacaaca aagggggaga tttgtatgaa agtttggctg gttggtgcct 50

<210> SEQ ID NO 13
<211> LENGTH: 51
<212> TYPE: DNA
<213> ORGANISM: Artificial Sequence
<220> FEATURE:
<223> OTHER INFORMATION: Primer

<400> SEQUENCE: 13
agcttgagct cgactctaga ggatccttat ttcaggttgc tataccattc t 51

<210> SEQ ID NO 14
<211> LENGTH: 51
<212> TYPE: DNA
<213> ORGANISM: Artificial Sequence
<220> FEATURE:
<223> OTHER INFORMATION: Primer

<400> SEQUENCE: 14
agaatggtat agcaacctga aataaggatc ctctagagtc gagctcaagc t 51

<210> SEQ ID NO 15
<211> LENGTH: 50
<212> TYPE: DNA
<213> ORGANISM: Artificial Sequence
<220> FEATURE:
<223> OTHER INFORMATION: Primer

<400> SEQUENCE: 15
aggcaccaac cagccaaact ttcatacaaa tctccccctt tgttgtttct 50

<210> SEQ ID NO 16
<211> LENGTH: 50
<212> TYPE: DNA
<213> ORGANISM: Artificial Sequence
<220> FEATURE:
<223> OTHER INFORMATION: Primer

<400> SEQUENCE: 16
gaaagcgagt atccagacgc agcatacaaa tctccccctt tgttgtttct 50

<210> SEQ ID NO 17
<211> LENGTH: 50

<212> TYPE: DNA
<213> ORGANISM: Artificial Sequence
<220> FEATURE:
<223> OTHER INFORMATION: Primer

<400> SEQUENCE: 17
agaaacaaca aagggggaga tttgtatgtt caagccgaaa gcgatcgcgg 50

<210> SEQ ID NO 18
<211> LENGTH: 50
<212> TYPE: DNA
<213> ORGANISM: Artificial Sequence
<220> FEATURE:
<223> OTHER INFORMATION: Primer

<400> SEQUENCE: 18
agcttgagct cgactctaga ggatccttaa cgcagcaggc ccagaaactg 50

<210> SEQ ID NO 19
<211> LENGTH: 50
<212> TYPE: DNA
<213> ORGANISM: Artificial Sequence
<220> FEATURE:
<223> OTHER INFORMATION: Primer

<400> SEQUENCE: 19
cagtttctgg gcctgctgcg ttaaggatcc tctagagtcg agctcaagct 50

<210> SEQ ID NO 20
<211> LENGTH: 50
<212> TYPE: DNA
<213> ORGANISM: Artificial Sequence
<220> FEATURE:
<223> OTHER INFORMATION: Primer

<400> SEQUENCE: 20
ccgcgatcgc tttcggcttg aacatacaaa tctccccctt tgttgtttct 50

<210> SEQ ID NO 21
<211> LENGTH: 50
<212> TYPE: DNA
<213> ORGANISM: Artificial Sequence
<220> FEATURE:
<223> OTHER INFORMATION: Primer

<400> SEQUENCE: 21
agaaacaaca aagggggaga tttgtatggt gaacgtttcc aatgccgttg 50

<210> SEQ ID NO 22
<211> LENGTH: 66
<212> TYPE: DNA
<213> ORGANISM: Artificial Sequence
<220> FEATURE:
<223> OTHER INFORMATION: Primer

<400> SEQUENCE: 22
cgaaggtacc aaacagtttg cccattttga attcctcctt ttcagtcaag tcccttccac 60
ttgacc 66

<210> SEQ ID NO 23
<211> LENGTH: 66
<212> TYPE: DNA
<213> ORGANISM: Artificial Sequence
<220> FEATURE:
<223> OTHER INFORMATION: Primer

<400> SEQUENCE: 23
ggtcaagtgg aagggacttg actgaaaagg aggaattcaa aatgggcaaa ctgtttggta 60
ccttcg 66

<210> SEQ ID NO 24
<211> LENGTH: 66
<212> TYPE: DNA
<213> ORGANISM: Artificial Sequence
<220> FEATURE:
<223> OTHER INFORMATION: Primer

<400> SEQUENCE: 24
gaaagcgagt atccagacgc agcattttga attcctcctt tttaaccttt cagtgcttct 60
tccagc 66

<210> SEQ ID NO 25
<211> LENGTH: 66
<212> TYPE: DNA
<213> ORGANISM: Artificial Sequence
<220> FEATURE:
<223> OTHER INFORMATION: Primer

<400> SEQUENCE: 25
gctggaagaa gcactgaaag gttaaaaagg aggaattcaa aatgctgcgt ctggatactc 60
gctttc 66

<210> SEQ ID NO 26
<211> LENGTH: 66
<212> TYPE: DNA
<213> ORGANISM: Artificial Sequence
<220> FEATURE:
<223> OTHER INFORMATION: Primer

<400> SEQUENCE: 26
ttttcagcgg atgttcggtg ttcattttga attcctcctt ttcaaccagc caggcgttta 60
cgagtc 66

<210> SEQ ID NO 27
<211> LENGTH: 66
<212> TYPE: DNA
<213> ORGANISM: Artificial Sequence
<220> FEATURE:
<223> OTHER INFORMATION: Primer

<400> SEQUENCE: 27
gactcgtaaa cgcctggctg gttgaaaagg aggaattcaa aatgaacacc gaacatccgc 60
tgaaaa 66

<210> SEQ ID NO 28
<211> LENGTH: 67
<212> TYPE: DNA
<213> ORGANISM: Artificial Sequence
<220> FEATURE:
<223> OTHER INFORMATION: Primer

<400> SEQUENCE: 28
accgcgatcg ctttcggctt gaacattttg aattcctcct ttttaaatca gtttgaattc 60
accgctg 67

<210> SEQ ID NO 29
<211> LENGTH: 67

```
<212> TYPE: DNA
<213> ORGANISM: Artificial Sequence
<220> FEATURE:
<223> OTHER INFORMATION: Primer

<400> SEQUENCE: 29

cagcggtgaa ttcaaactga tttaaaaagg aggaattcaa aatgttcaag ccgaaagcga     60

tcgcggt                                                               67


<210> SEQ ID NO 30
<211> LENGTH: 51
<212> TYPE: DNA
<213> ORGANISM: Artificial Sequence
<220> FEATURE:
<223> OTHER INFORMATION: Primer

<400> SEQUENCE: 30

gcttgagctc gactctagag gatccttaac gcagcaggcc cagaaactgc a              51


<210> SEQ ID NO 31
<211> LENGTH: 51
<212> TYPE: DNA
<213> ORGANISM: Artificial Sequence
<220> FEATURE:
<223> OTHER INFORMATION: Primer

<400> SEQUENCE: 31

tgcagtttct gggcctgctg cgttaaggat cctctagagt cgagctcaag c              51


<210> SEQ ID NO 32
<211> LENGTH: 50
<212> TYPE: DNA
<213> ORGANISM: Artificial Sequence
<220> FEATURE:
<223> OTHER INFORMATION: Primer

<400> SEQUENCE: 32

caacggcatt ggaaacgttc accatacaaa tctccccctt tgttgtttct                50
```